US009784723B1

(12) United States Patent
Oxley et al.

(10) Patent No.: US 9,784,723 B1
(45) Date of Patent: Oct. 10, 2017

(54) SYSTEMS AND METHODS FOR PROVIDING NON-DETONATABLE EXPLOSIVES OR EXPLOSIVE STIMULANT SOURCES

(71) Applicant: Board of Governors for Higher Education, State of Rhode Island and Providence Plantations, Providence, RI (US)

(72) Inventors: Jimmie C. Oxley, Narragansett, RI (US); James L. Smith, Narragansett, RI (US); Jonathan N. Canino, Kingston, RI (US)

(73) Assignee: Council on Postsecondary Education, Warwick, RI (US)

( * ) Notice: Subject to any disclaimer, the term of this patent is extended or adjusted under 35 U.S.C. 154(b) by 0 days.

(21) Appl. No.: 14/215,768

(22) Filed: Mar. 17, 2014

Related U.S. Application Data

(60) Provisional application No. 61/790,014, filed on Mar. 15, 2013.

(51) Int. Cl.
*G01N 31/00* (2006.01)
*C06B 21/00* (2006.01)
*G01N 33/22* (2006.01)

(52) U.S. Cl.
CPC .......... *G01N 33/227* (2013.01); *Y10T 436/10* (2015.01)

(58) Field of Classification Search
CPC ........ G01N 33/27; G01N 33/52; G01N 31/22; C06B 23/00; C09K 11/00; C09K 11/04
USPC ....................................... 252/408.1
See application file for complete search history.

(56) References Cited

U.S. PATENT DOCUMENTS

| | | | |
|---|---|---|---|
| 5,359,936 A | 11/1994 | Simpson et al. | |
| 5,413,812 A | 5/1995 | Simpson et al. | |
| 5,648,636 A | 7/1997 | Simpson et al. | |
| 7,694,628 B2 | 4/2010 | Adebimpe et al. | |
| 7,932,089 B2 | 4/2011 | Cohen-Arazi et al. | |
| 8,173,430 B2 | 5/2012 | Cohen-Arazi et al. | |
| 2005/0016675 A1* | 1/2005 | Bain | B60J 10/0088 156/293 |
| 2006/0099247 A1* | 5/2006 | Cantwell | A61M 15/00 424/451 |
| 2007/0221087 A1* | 9/2007 | Adebimpe | A01K 15/02 102/355 |
| 2009/0194744 A1 | 8/2009 | Adebimpe | |
| 2009/0199936 A1 | 8/2009 | Hagit et al. | |

* cited by examiner

*Primary Examiner* — Jill Warden
*Assistant Examiner* — Julie Tavares
(74) *Attorney, Agent, or Firm* — Gesmer Updegrove LLP

(57) ABSTRACT

A non-detonable source of at least one of an explosive or explosive vapor is disclosed, as well as a method of preparing the explosive or explosive vapor that includes the step of mixing the explosive with at least 50% inert material which retains the explosive vapor until heat is applied.

12 Claims, 31 Drawing Sheets

Table 1 - Microsphere bake conditions

| Polymer | Hot Dry (°C) | Purification (°C) |
|---|---|---|
| Poly(4-methylstyrene) (P4MS) | 60 | - |
| Polymethylmethacyrlate (PMMA) | 60 | - |
| Polystyrene (PS) | 80 | 150 |
| Polycarbonate (PC) | 80 | - |
| Polysulfone (PSf) | 120 | - |
| Polyetherimide (PEI) | 120 | - |

FIG. 21

Table 2 – Polymer Tg and Release Temperature

| Polymer | Tg 20°C/min (°C) | TATP Start Loss 2°C/min (°C) | TATP Max Loss 2°C/min (°C) | TATP Max Loss 20°C/min (°C) | DSC Max Endotherm 20°C/min (°C) TATP | DSC Max Exotherm 20°C/min (°C) TATP | DSC Max Endotherm 20°C/min (°C) DADP | DSC Max Exotherm 20°C/min (°C) DADP | DADP Start Loss 2°C/min (°C) | DADP Max Loss 2°C/min (°C) | Polymer Decomp (°C) | Release Type |
|---|---|---|---|---|---|---|---|---|---|---|---|---|
| Triacetonetriperoxide (TATP) | - | - | - | - | 98 | 238 | - | - | - | - | - | - |
| Diacetonediperoxide (DADP) | - | - | - | - | - | - | 133 | 253 | - | - | - | - |
| Poly(D,L-lactide-co-glycolide) (PLGA) | 45-50* | ~46, 60 | - | - | - | - | - | - | - | - | - | A** |
| Polyethylmethacrylate (PEM) | 63* | 65 | 142 | - | - | - | - | - | - | - | - | B |
| Poly (vinyl butyral-co-vinyl alcohol-co-vinyl acetate) (PVBVAVA) | 64 | 77 | 93 | 102 | 89 | - | - | - | - | - | - | A |
| Poly(4-methyl styrene) (P4MS) | 104* | 75 | ~124, 190 | - | - | - | - | - | - | - | - | A |
| Polymethylmethacrylate (PMMA) | 105* | 77 | 154 | - | - | - | - | - | - | - | - | B |
| Polystyrene (PS) | 109 | 77 | 152 | 163 | 63 | 231 | - | - | - | - | - | A |
| Polycarbonate (PC) | 148 | 88 | 135 | 168 | 87 | - | 132 | - | 103, 134 | 160 | 443* | A |
| Polysulfone (PSf) | 190 | 139 | 167 | 183 | 93 | 184 | - | - | - | - | 480-485* | C |
| Polyetherimide (PEI) | 220 | 140 | 195 | 197 | 93 | 199 | - | - | 149 | 197 | 530-535* | C |

* Literature Value    *** Polymer Decomposes at Room Temperature

FIG. 22

Table 3

| All samples baked at 80°C for 24 hours | | |
|---|---|---|
| Sample | % TATP | Std Dev |
| Polystyrene | 19.1 | 1.0 |
| Polycarbonate | 19.2 | 2.0 |
| Blanks | % Mass Lost | Std Dev |
| Blank PS | 0.25 | 0.04 |
| Blank PC | 0.17 | 0.008 |

FIG. 23

Table 4 – Storage Stability

| Polymer | % TATP Initial | 238 Days | 322 Days | 432 Days | 466 Days | 771 Days | 873 Days |
|---|---|---|---|---|---|---|---|
| Polystyrene | 16.0 | - | - | 15.8 | - | - | 15.9 |
| Polysulfone | 19.7 | - | 19.6 | - | - | 19.6 | - |
| Polycarbonate | 18.7 | 18.5* | - | - | 18.3* | - | - |

*Determined by accelerated aging at 70°C

SYSTEMS AND METHODS FOR PROVIDING NON-DETONATABLE EXPLOSIVES OR EXPLOSIVE STIMULANT SOURCES

PRIORITY

The present application claims priority to U.S. Provisional Patent Application Ser. No. 61/790,014 filed Mar. 15, 2013, the disclosure of which is hereby incorporated by reference in its entirety.

GOVERNMENT SUPPORT

The present invention was developed, in part, with support from the United States government under Grant No. HSHQDC-10-000197 from the Department of Homeland Security, and the United States government has certain rights to this invention.

BACKGROUND

This invention creates simulant materials that supply a characteristic headspace (vapor) signature of explosives. The invention could be used in training, such as the training of detecting dogs, or for calibration and benchmarking, such as for analytical instrumentation. The simulant materials are safe for handling and storage being non-detonable and non-explosive.

With the increase in terrorist activities, legitimate demand for access to explosives or explosive signature material has come from law enforcement agencies and from private entities training detection canines or calibrating or creating libraries for explosive detection instrumentation. Many explosives are too hazardous to handle by routine trainers or instrumentation personnel or the facility where such handling would take place is not licensed or appropriately protected to acquire or store such hazardous material.

U.S. Pat. Nos. 5,359,936, 5,413,812, and 5,648,636 from Lawrence Livermore National Laboratory disclose explosive simulants comprising a quantity of an explosive material and a quantity of a non-explosive material mix in proportions such that it produces at least the scent and elemental equivalents to said explosive material, without being capable of detonating. These patents state they are not applicable to primary explosives. It is claimed that the simulants to give off signature vapor at room temperature. Since the product releases vapor at room temperature, there is potential of cross-contamination during storage. Furthermore, these materials create explosive dust.

U.S. Pat. Nos. 7,932,089, and 8,173,430 as well as U.S. Patent Application Publication No. 2009/0199936 disclose simulants for primary explosives comprised of one part primary explosive material and one part inert, non-explosive compound. The inert compound can be a polymer, inert powder, or a mixture of both. The finished product is specified to be devoid of non-inherently associated volatiles and in the form of a homogenous, flexible, and non-particulate material. The product releases vapor at room temperature which leads to the potential of cross-contamination during storage.

US. Patents Application Publication No. 2009/0194744 and U.S. Pat. No. 7,694,628 disclose energetically-inert pseudo-scents of an explosive comprising among other things a non-energetic component having similar electronic properties and a de-energized derivative of an energetic material. The disclosed claim of the need for matched electronic properties and de-energized explosives is not relevant to producing simulant scents.

There remains a need therefore, for a safe form of the hazardous material that is non-explosive and may be safely shipped and handled by canine trainers and instrument manufacturers.

SUMMARY

In accordance with an embodiment, the invention provides a non-detonable source of at least one of an explosive or explosive vapor. In accordance with a further embodiment, the invention provides a method of preparing the explosive or explosive vapor that includes the step of mixing the explosive with at least 50% inert material which retains the explosive vapor until heat is applied.

In accordance with a further embodiment, the invention provides a non-detonable explosive vapor sources consisting of an explosive (at the 5 to 50%) encapsulated in a polymer which retains the explosive vapor until heat is applied.

In accordance with a further embodiment, the invention provides a method of creating a vapor signature for explosives using the volatile components always found in the headspace of the explosive. In accordance with a further embodiment, the invention provides a vapor signature simulant for HMTD using non-explosive chemicals dimethylamine (DMA) and trimethylamine TMA.

In accordance with a further embodiment, the invention provides a vapor signature simulant for HMTD using dimethylamine (DMA) in the range of 5 to 100% and trimethylamine TMA in the range of 0 to 55% and this mixture dispersed in water so that water makes up 1 to 95%.

BRIEF DESCRIPTION OF THE DRAWINGS

The following description will be further understood with reference to the accompanying drawings in which:

FIG. 21 shows Table 1 showing microsphere bake conditions in accordance with an embodiment of the invention;

FIG. 22 shows Table 2 showing polymer Tg and release temperatures in a system in accordance with an embodiment of the invention;

FIG. 23 shows Table 3 showing percent TATP and percent mass lost for various samples baked at 80° C. for 24 hours in accordance with an embodiment of the invention; and FIG. 24 shows Table 4 showing storage stability characteristics for various samples in accordance with an embodiment of the invention.

The drawings are shown for illustrative purposes only.

DETAILED DESCRIPTION

The invention is a non-explosive matrix, which upon heating, provides a vapor simulating the headspace signature of an explosive. This headspace signature is created by dispersing an explosive or the materials that comprise some or the entire headspace signature of an explosive in an inert matrix material, such as a polymer. The amount of explosive material contained in the matrix material is controlled to render the explosive non-detonable and non-explosive, at less than 50% by weight. The matrix material must be thermally stable (not decompose) up to or past its own melting point and be chemically inert with the explosive or explosive vapor components contained.

Figures 1A, 1B:
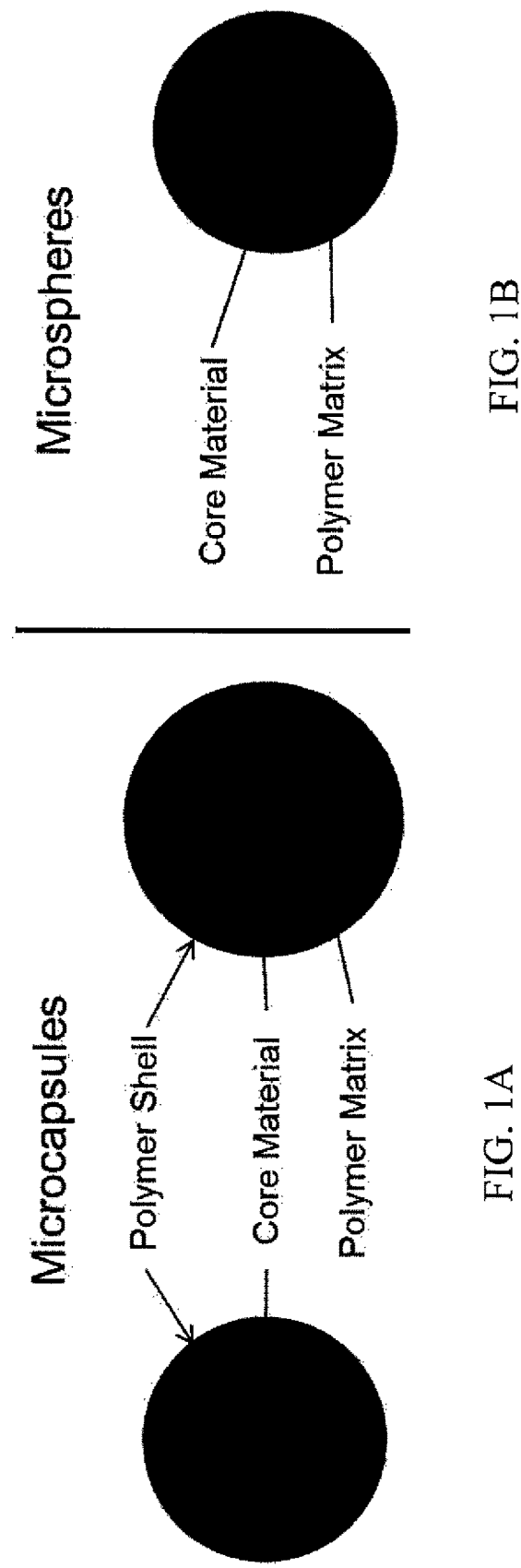
FIGS. 1A and 1B show illustrative diagrammatic views of microcapsules and microspheres in accordance with various embodiments of the present invention.

The invention utilizes plastic microspheres or microcapsules that contain an amount of the actual explosive or the elements of the characteristic explosive headspace (vapor) signature. The actual explosive is encased in a shell material of plastic, either in microcapsules or microspheres. A microsphere has a polymer (shell material) with the desired core material dispersed through it (as shown in FIG. 1A). Typically, they have maximum loadings of core material between 20% and 30%, with 2-5% on the surface of the sphere. Microcapsules have a discrete polymer shell which is surrounding either pure core material or a microsphere-like matrix of polymer and core material (As shown in FIG. 1B). This allows microcapsules much higher loadings of core material than microspheres.

For applications as a vapor source (canine training aids or vapor standards for detection instrumentation), it is preferred that polymer be should not have a significant vapor signature. This usually means the polymer should be free of short chain impurities, residual plasticizers, or decomposition upon heating.

For simulants containing no actual explosive it may be possible to provide a bottle or other container.

Example 1: Polystyrene and TATP Using DCM and Water with Polyvinyl Alcohol

Polystyrene shell material (1 g) was added with stirring to 10 mL of the dispersed phase solvent dichloromethane (DCM). Once all the shell material had dissolved 250 mg of the explosive, triacetone triperoxide (TATP), was added. When the TATP had completely dissolved in the polymer solution, the entire solution was added to a 2 L beaker containing 200 mL water with 2% of polyvinyl alcohol which was being stirrer at ~900 rpm. This emulsion mixture was allowed to stir until the DCM evaporated allowing the formation of solid plastic microspheres (~1 hr). Additional water (~400 mL) was added with stirring to aid filtration. The solid microspheres were recovered by vacuum filtration. Residual polyvinyl alcohol was removed by further rinsing with distilled water (at least 1 L). The microspheres were dried by under air until they ceased to clump together. The spheres were placed in an open container and baked at 70° C. overnight to remove any remaining solvent.

Figure 2A:
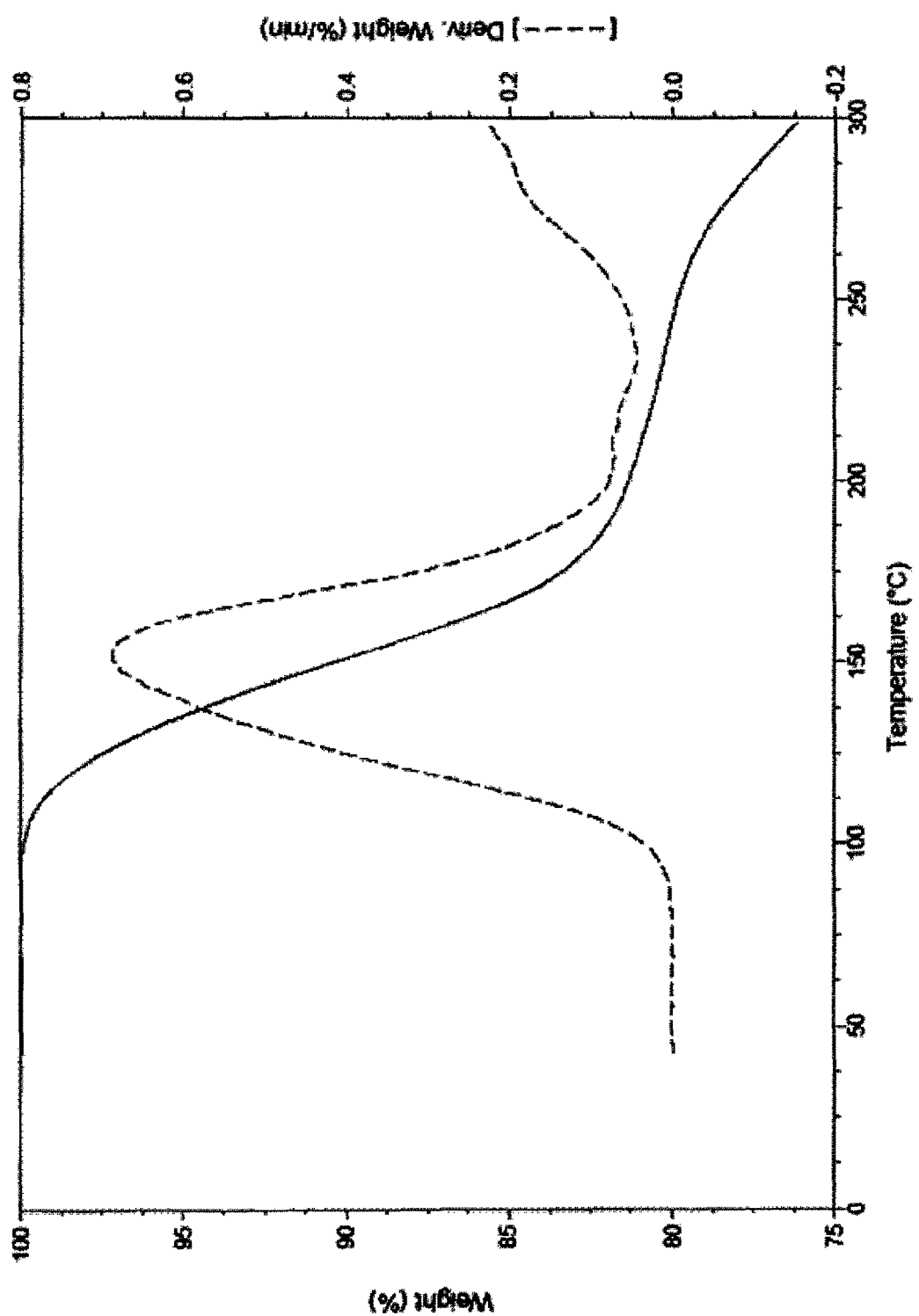
FIGS. 2A and 2B show illustrative graphical representations of TGA of PS (polystyrene)-TA-TATP microspheres trace (solid) and TGA derivative (dotted) at 2°/min (FIG. 2A) and 20°/min (FIG. 2B)
Figure 2B:
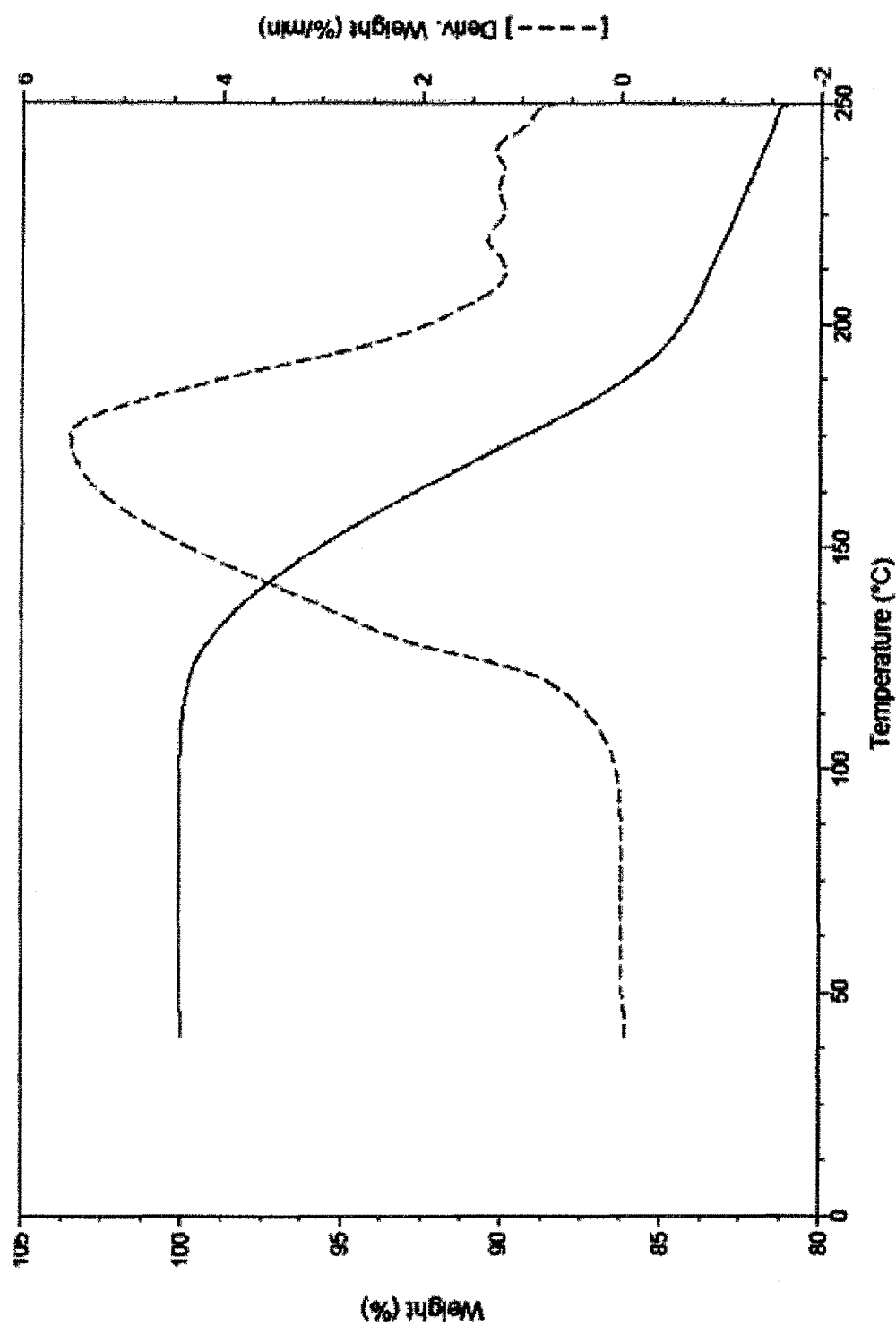
Figure 3:
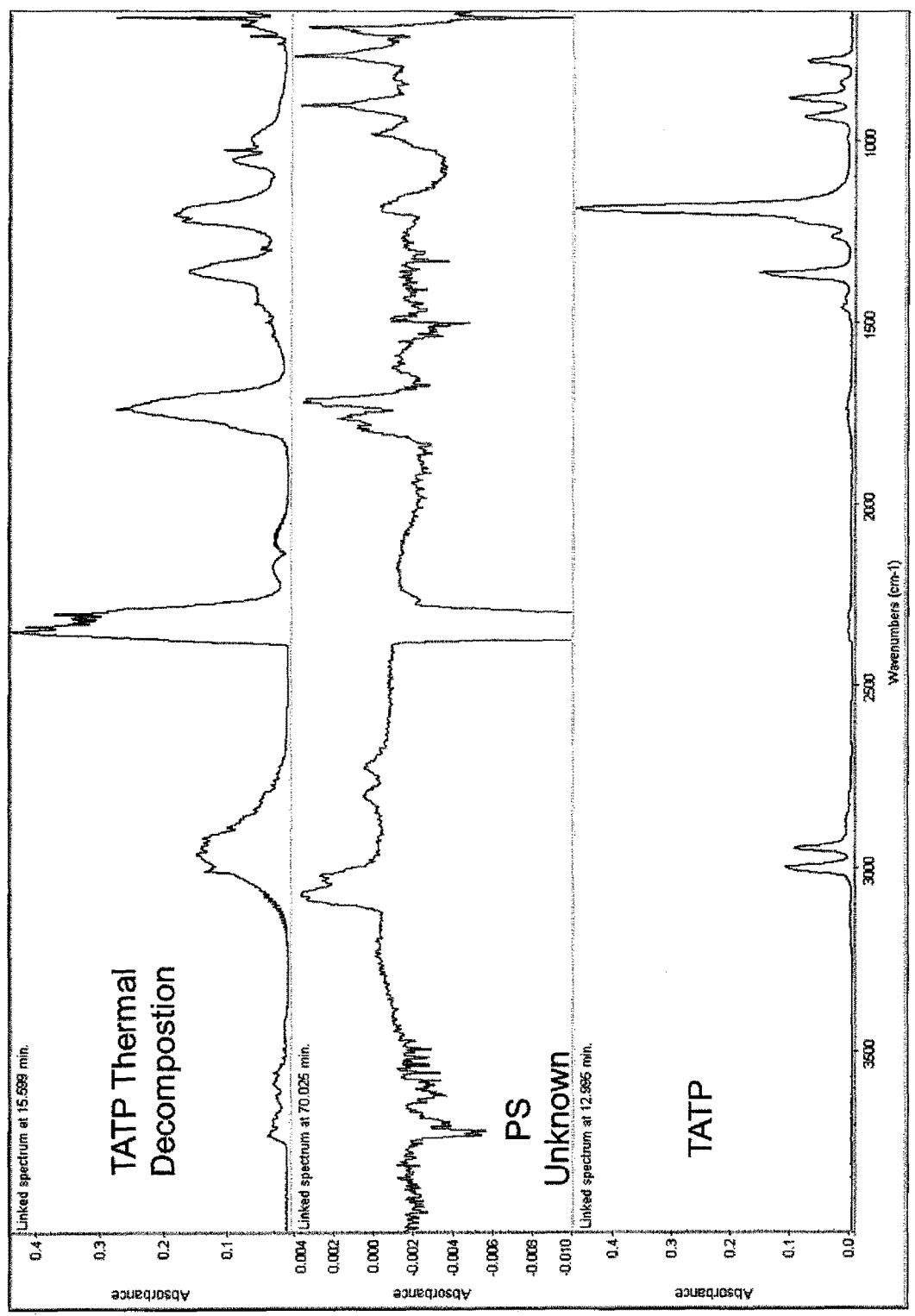
FIG. 3 shows an illustrative graphical representation of a comparison of polystyrene unknown (middle) IR to pure TATP (bottom) & TATP decomposition (top)

FIGS. 2A and 2B show illustrative graphical representations of TGA of PS (polystyrene)-TA-TATP microspheres trace (solid) and TGA derivative (dotted) at 2°/min (FIG. 2A) and 20°/min (FIG. 2B). FIG. 3 shows an illustrative graphical representation of a comparison of polystyrene unknown (middle) IR to pure TATP (bottom) & TATP decomposition (top).

Figure 4A:
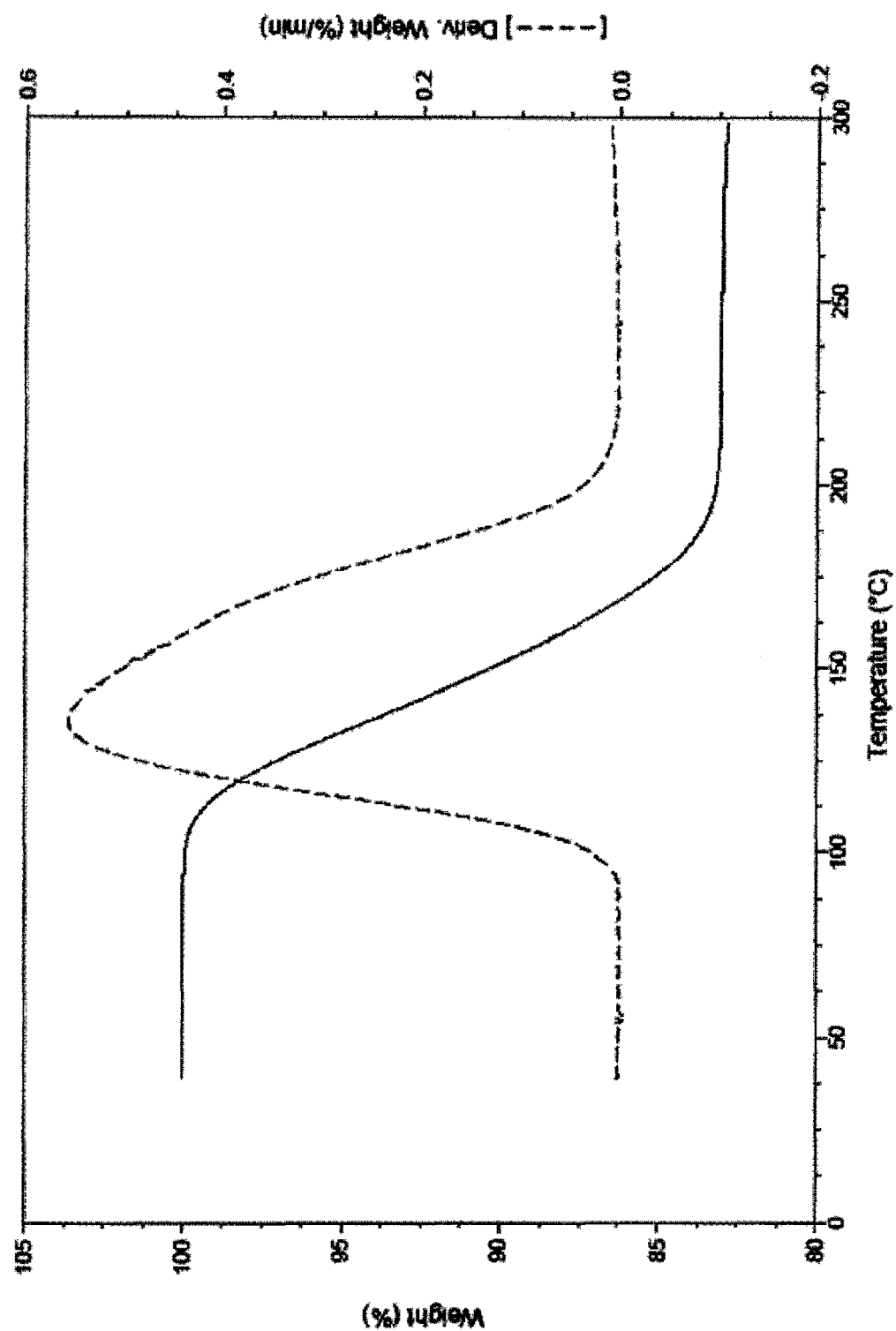
FIGS. 4A and 4B show illustrative graphical representations of TGA of PC-TATP microspheres trace (solid) and TGA derivative (dotted) at 2°/min (FIG. 4A) and 20°/min (FIG. 4B)
Figure 4B:
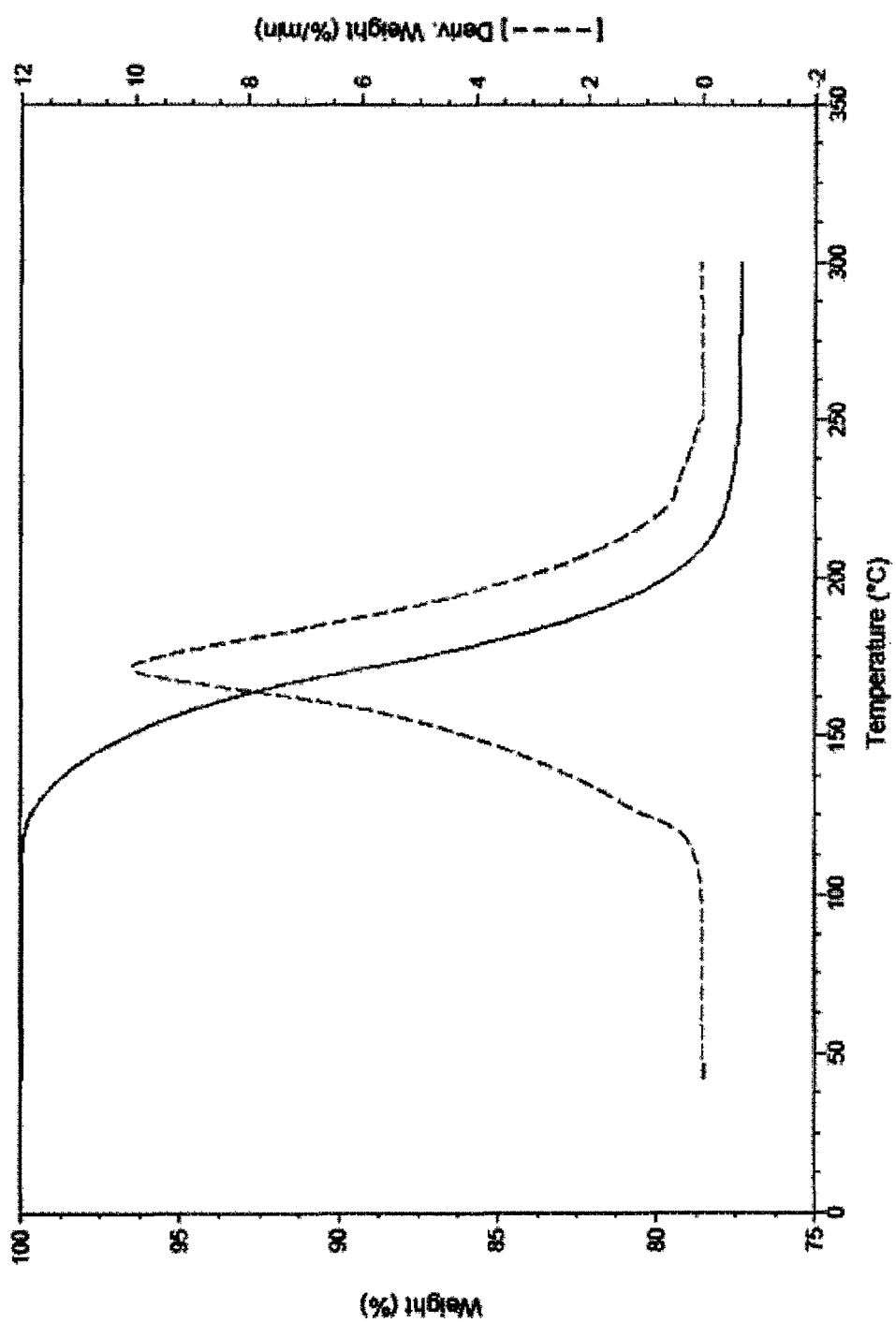
Figure 5:
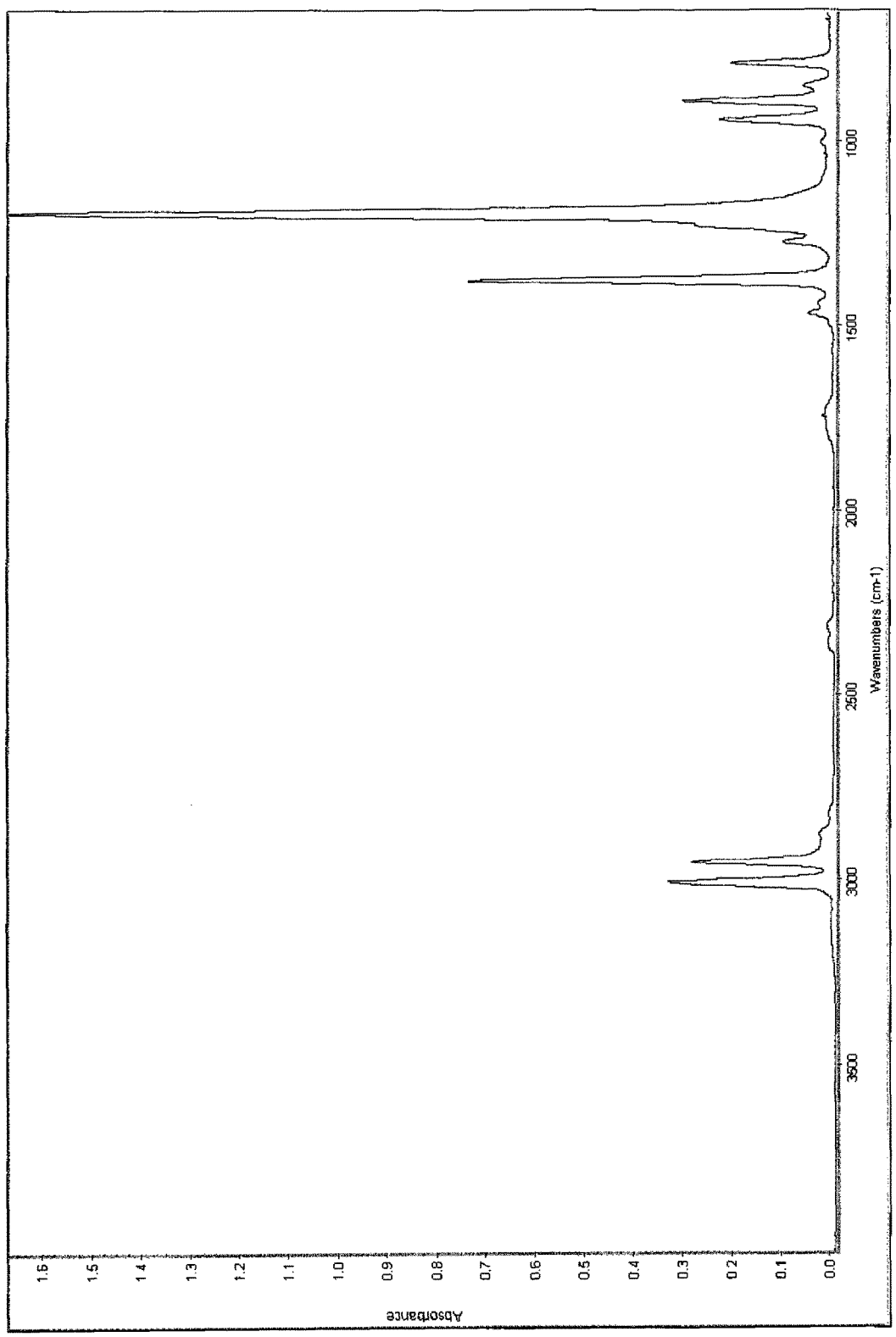
FIG. 5 shows an illustrative graphical representation of IR spectra of TATP from PC microspheres.

In comparison, with regard to PC (polycarbonate), FIGS. 4A and 4B show illustrative graphical representations of TGA of PC-TATP microspheres trace (solid) and TGA derivative (dotted) at 2°/min (FIG. 4A) and 20°/min (FIG. 4B). FIG. 5 shows an illustrative graphical representation of IR spectra of TATP from PC microspheres;

Example 2: Polysulfone and TATP Using Chloroform and Water with Polyvinyl Alcohol As above but polysulfone in chloroform was the initial dispersed phase, and the spheres were baked at 110° C. overnight to remove any remaining chloroform.

Figure 6A:
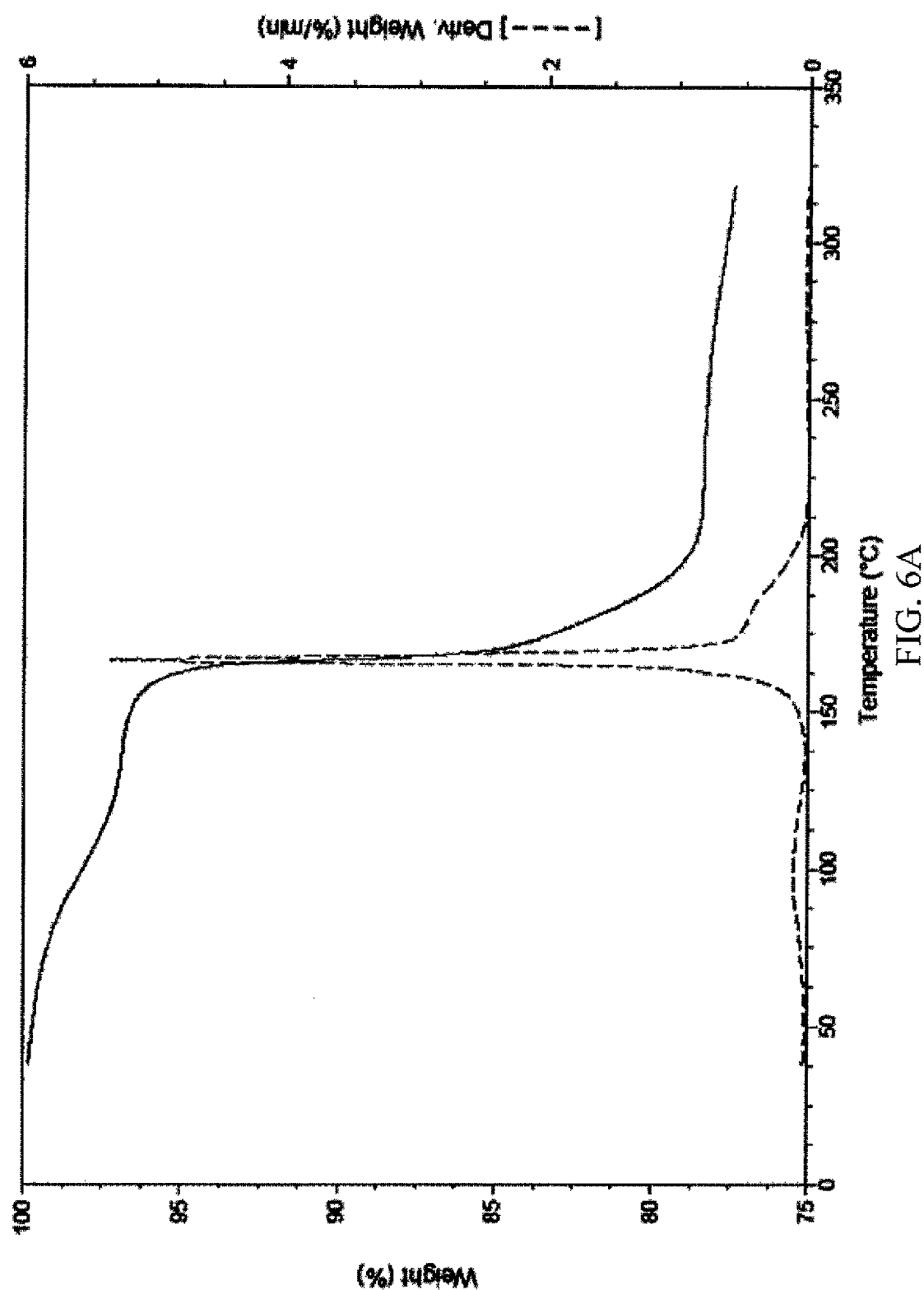
FIGS. 6A and 6B show illustrative graphical representations of TGA of PSf-TATP microspheres trace (solid) and TGA derivative (dotted) at 2°/min (FIG. 6A) and 20°/min (FIG. 6B)
Figure 6B:
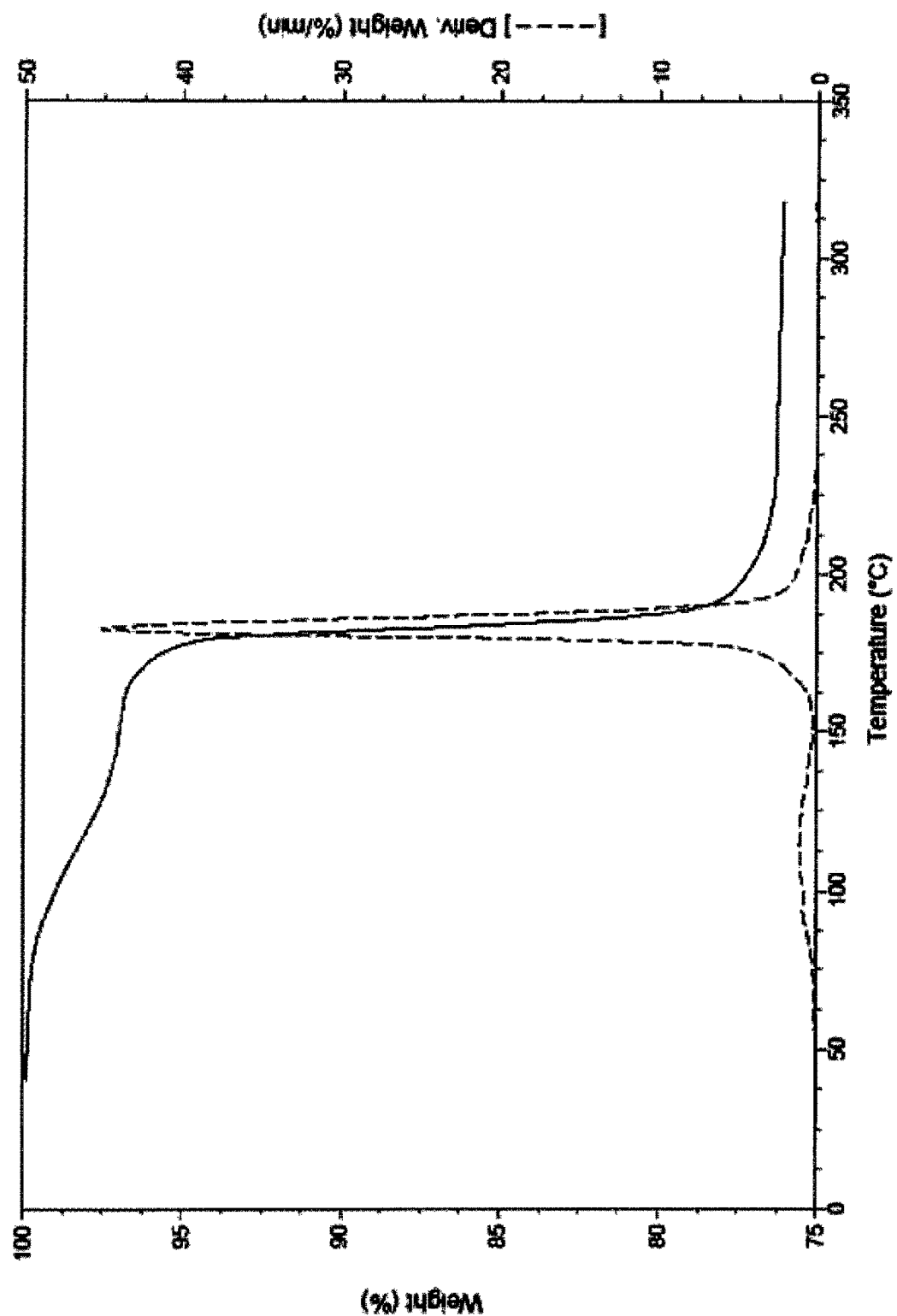
Figure 7:
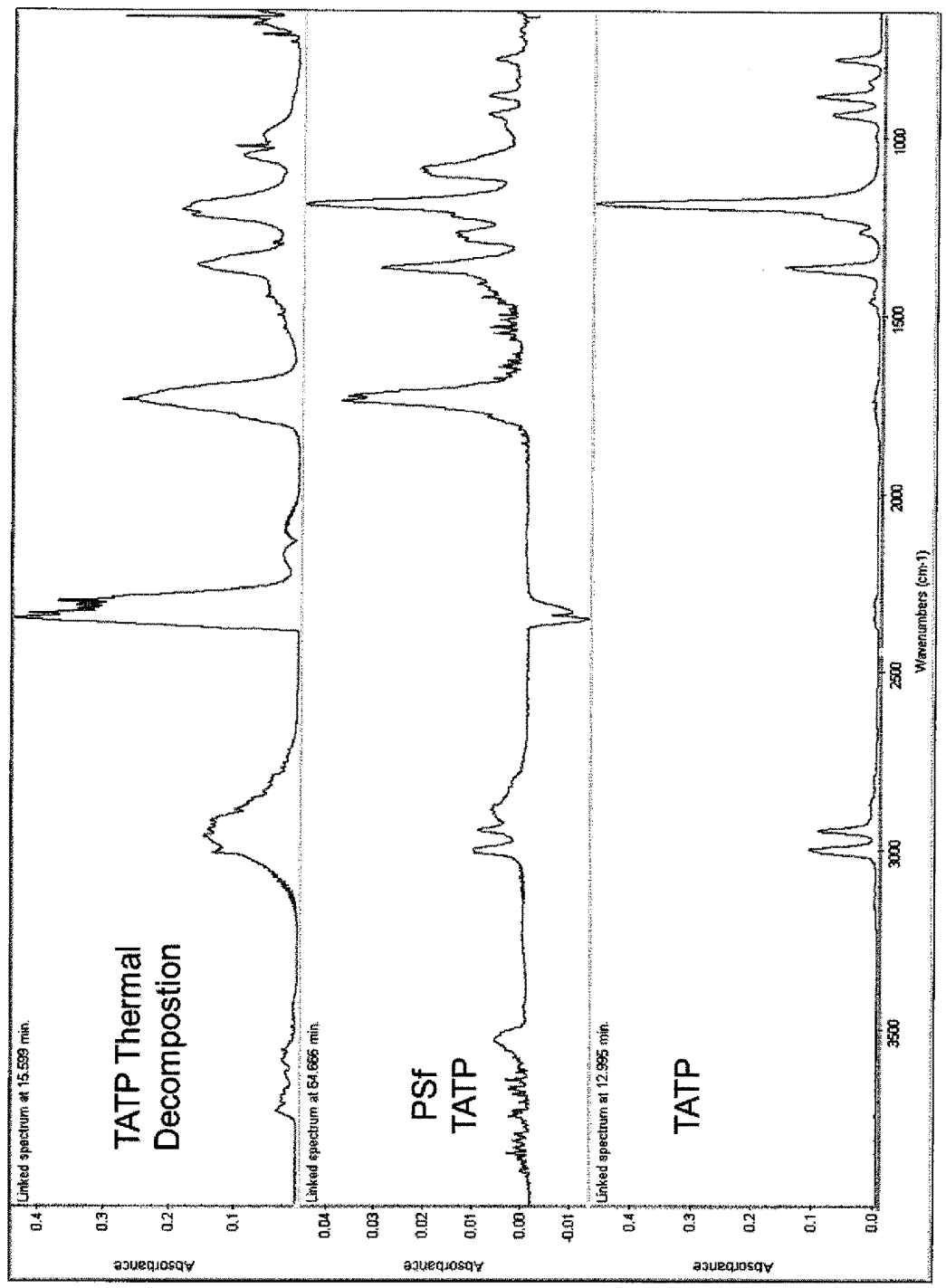
FIG. 7 shows an illustrative graphical comparisons of PSf-TATP (middle) IR to pure TATP (bottom) & TATP decomposition (top)
Figure 8A:
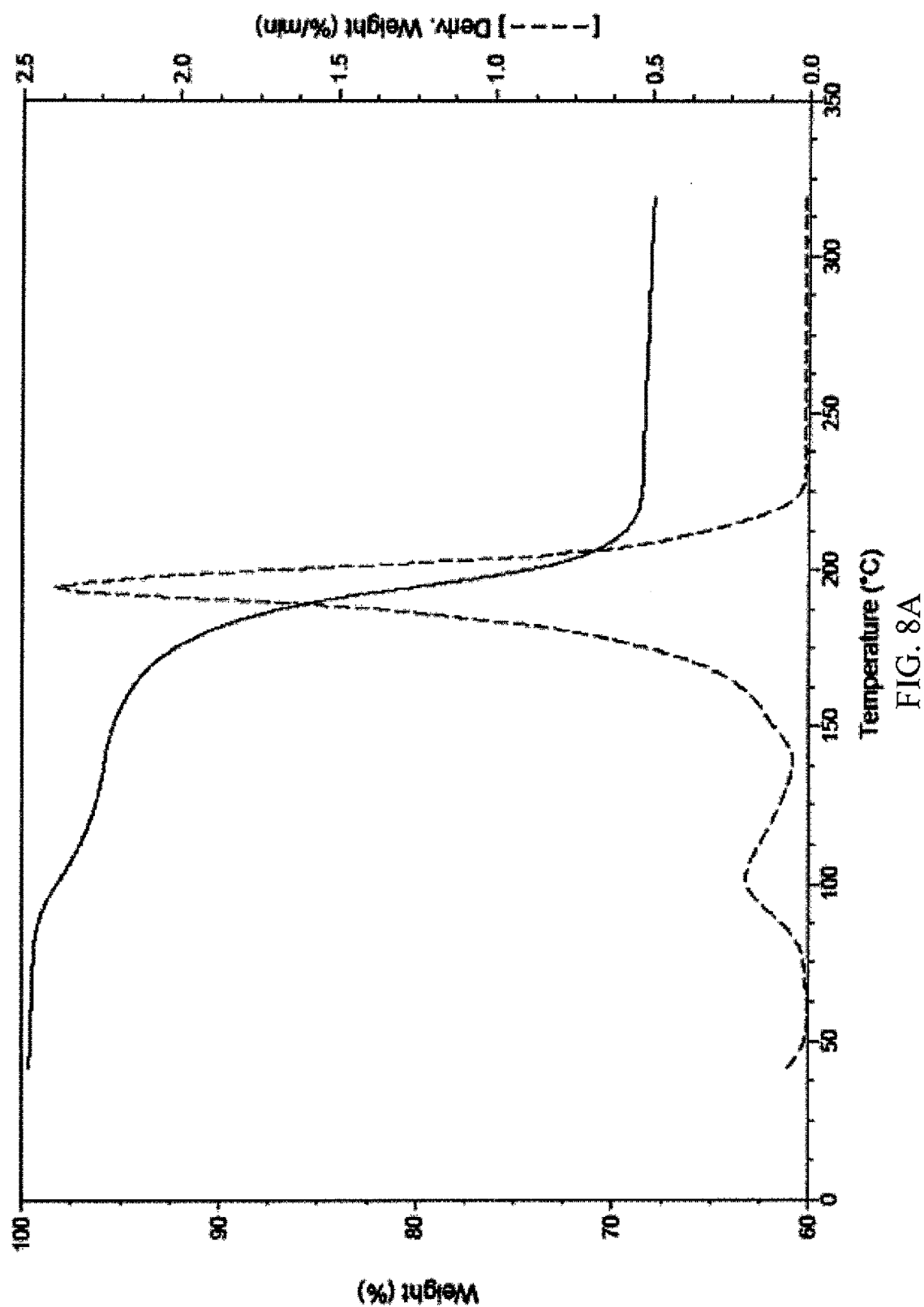
FIGS. 8A and 8B show illustrative graphical representations of TGA of PEI-TATP microspheres trace (solid) and TGA derivative (dotted) at 2°/min (FIG. 8A) and 20°/min (FIG. 8B)
Figure 8B:
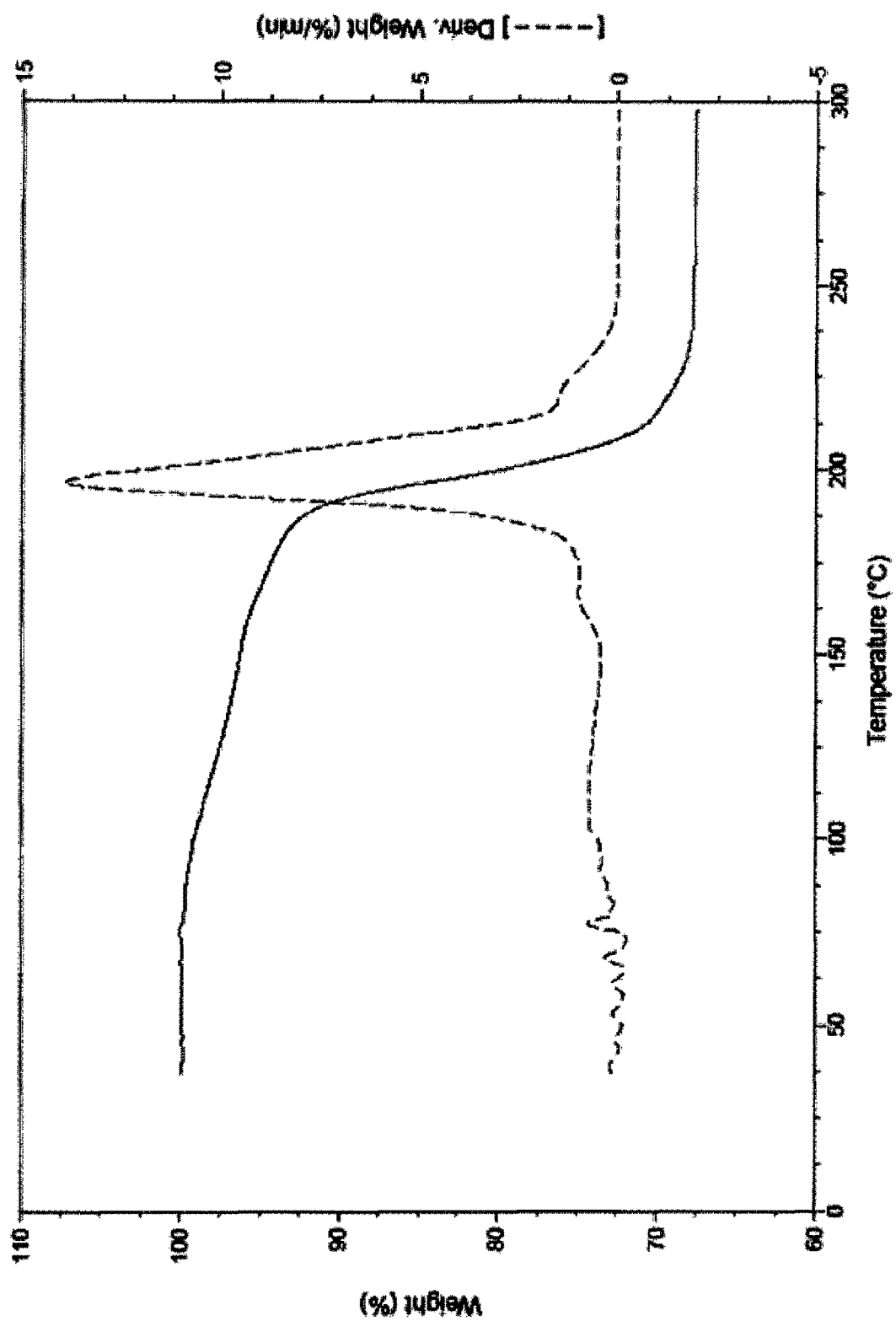
Figure 9:
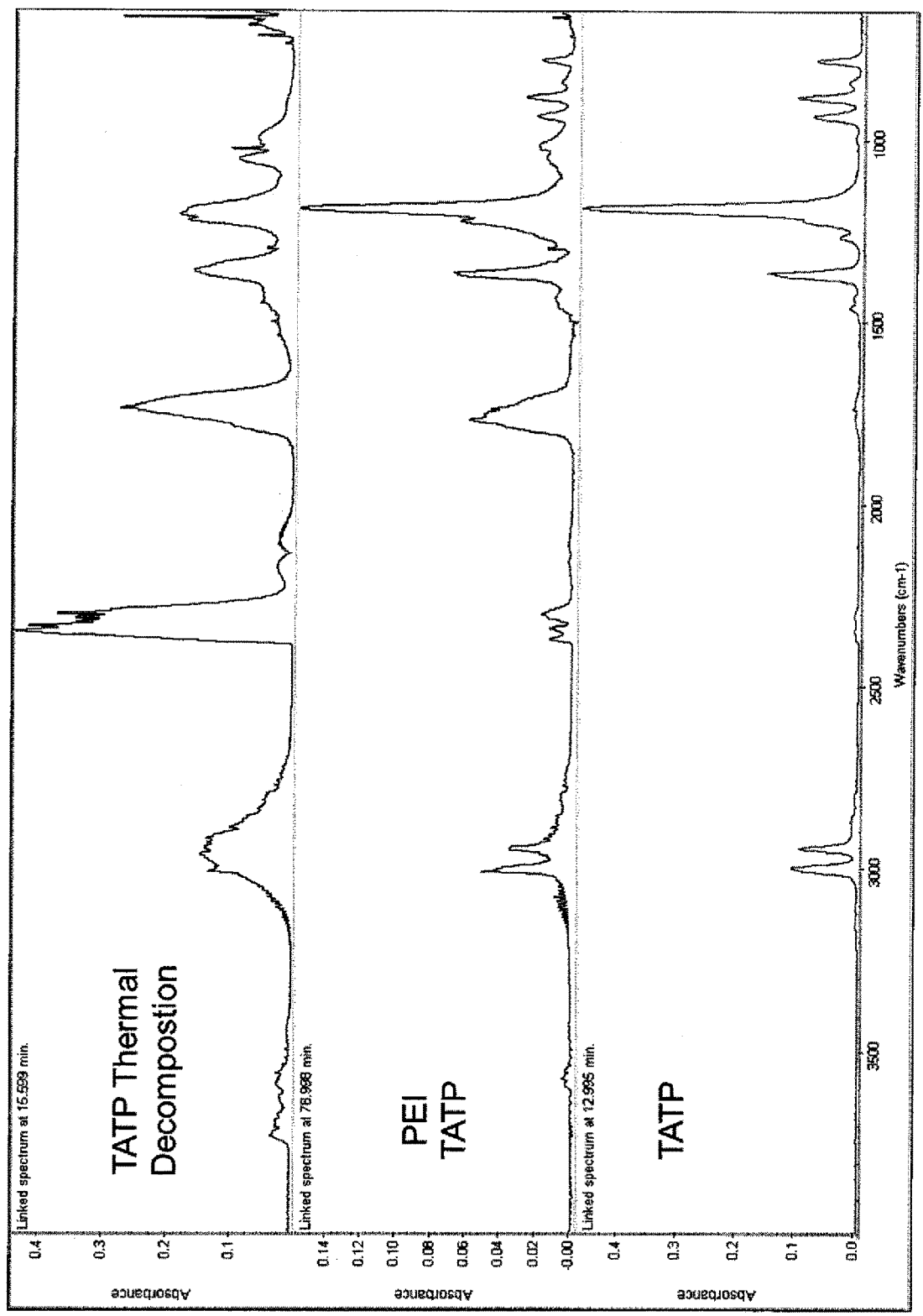
FIG. 9 shows an illustrative graphical comparisons of PEI-TATP (middle) IR to pure TATP (bottom) & TATP decomposition (top)

FIGS. 6A and 6B show illustrative graphical representations of TGA of PSf-TATP microspheres trace (solid) and TGA derivative (dotted) at 2°/min (FIG. 6A) and 20°/min (FIG. 6B). FIG. 7 shows an illustrative graphical comparisons of PSf-TATP (middle) IR to pure TATP (bottom) & TATP decomposition (top);

With regard to the use of polyetherimide (PEI), FIGS. 8A and 8B show illustrative graphical representations of TGA of PEI-TATP microspheres trace (solid) and TGA derivative (dotted) at 2°/min (FIG. 8A) and 20°/min (FIG. 8B). FIG. 9 shows an illustrative graphical comparisons of PEI-TATP (middle) IR to pure TATP (bottom) & TATP decomposition (top).

Figure 10:
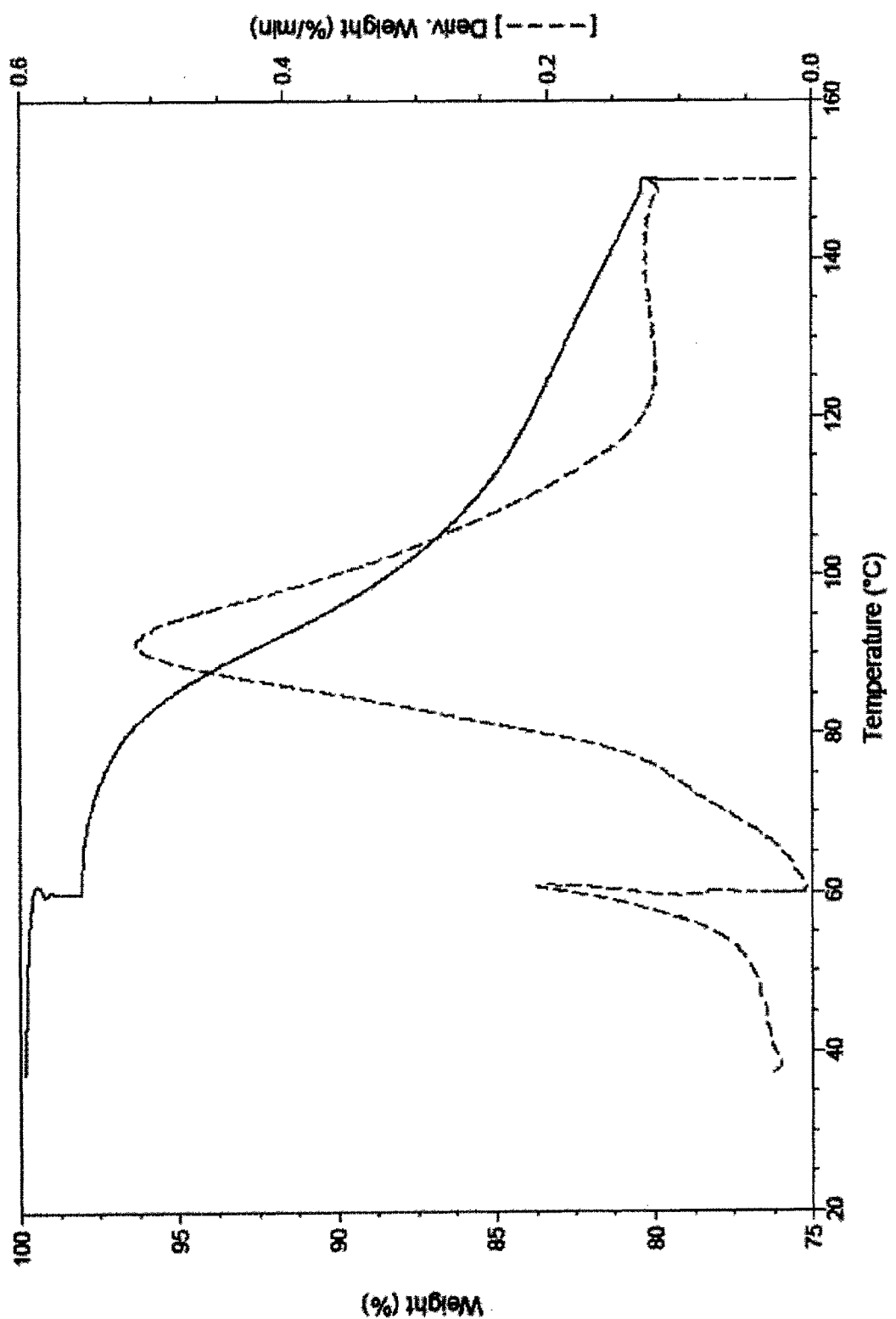
FIG. 10 shows an illustrative graphical representation of TGA of PLGA-TATP microspheres trace (solid) and TGA derivative (dotted line), at 2°/min.
Figure 11:
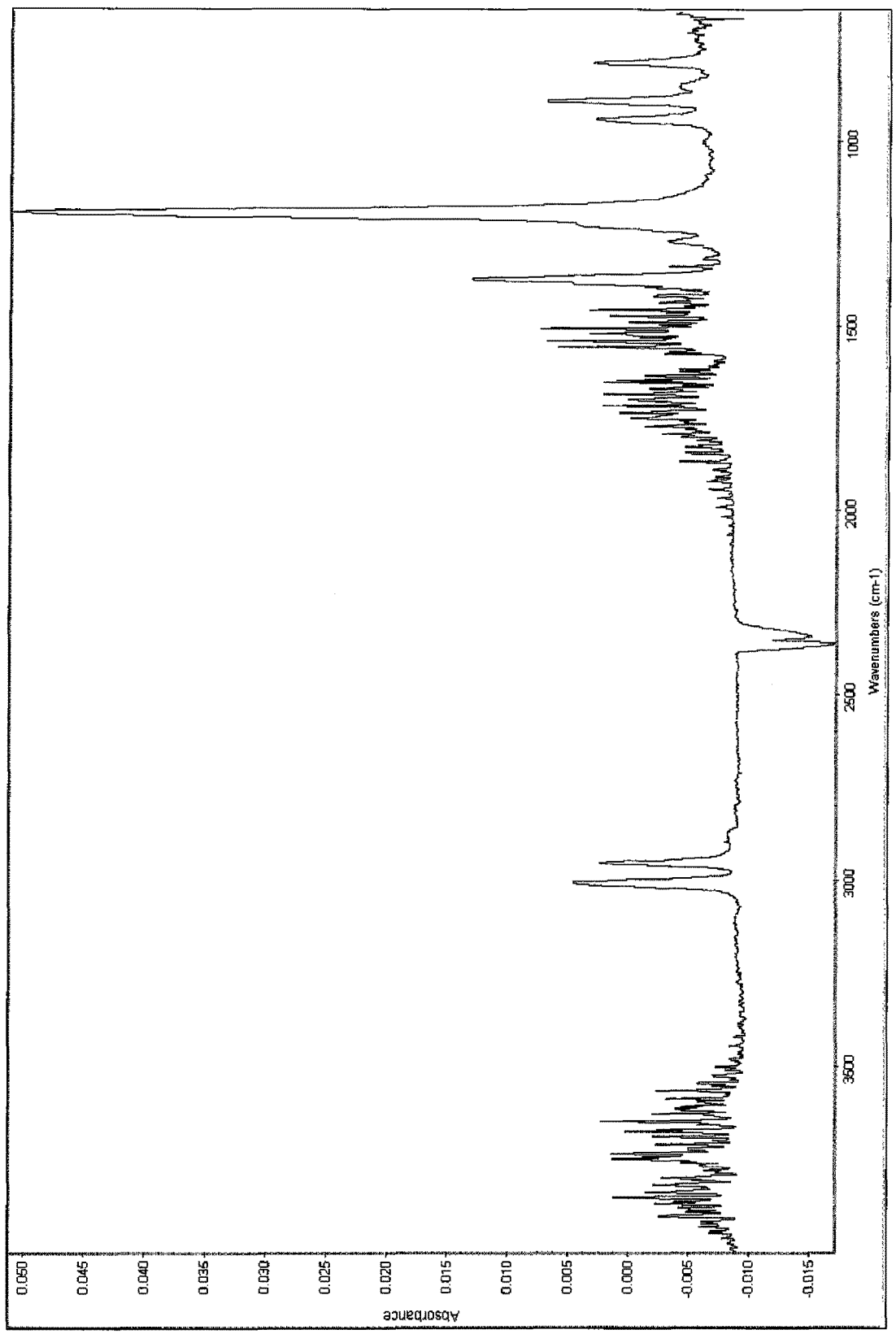
FIG. 11 shows an illustrative graphical representation of IR spectra of TATP from PLGA microspheres.

With regard to poly(lactic-co-glycolic acid) (PLGA), FIG. 10 shows an illustrative graphical representation of TGA of PLGA-TATP microspheres trace (solid) and TGA derivative (dotted line), at 2°/min. FIG. 11 shows an illustrative graphical representation of IR spectra of TATP from PLGA microspheres.

Example 3: Dip-Coating Polystyrene and Trinitrotoluene (TNT) Using Dichloromethane Polystyrene (1 g) was added with magnetic stirring to 10 mL of dichloromethane (DCM). Once all the polystyrene had dissolved, 250 mg of the explosive, trinitrotoluene (TNT), was added with continued stirring. The solution was allowed to stir for 5 minutes to allow for homogenous mixing then the magnetic stir bar was removed. The desired substrate (e.g. a glass slide or microheater) was dipped into the DCM solution and removed. This substrate was hung by the uncoated end in a fume hood to facilitate the evaporation of the DCM until the coating had solidified. The coated substrate was placed in an oven at 70° C. overnight to drive off the remaining DCM and fully cure the polystyrene coating.

Example 4: Vapor Simulant for Hexamethylene Triperoxide Diamine (HMTD)

An aqueous solution of dimethylamine (DMA) and trimethylamine TMA were prepared. Multiple dilutions were made to reduce the strong smell to a level typical of solid HMTD. Exemplary ratios are water (40-95%), TMA (5-50 wt %), DMF (0-55 wt %) and this mixture further diluted up to 100 fold.

The technique was applied to pre-made polymer such as polystyrene (PS), polysulfone (PSf), polyethylmethacrylate (PEM), poly(lactic-co-glycolic acid) (PLGA), polycarbonate (PC), polyetherimide (PEI), poly (vinyl butyral-co-vinyl alcohol-co-vinyl acetate) (PVBVAVA), polyethylmethacrylate (PEM). In some cases it was necessary to pre-heat the polymer to remove residual monomer and other volatile impurities.

Figure 12A:
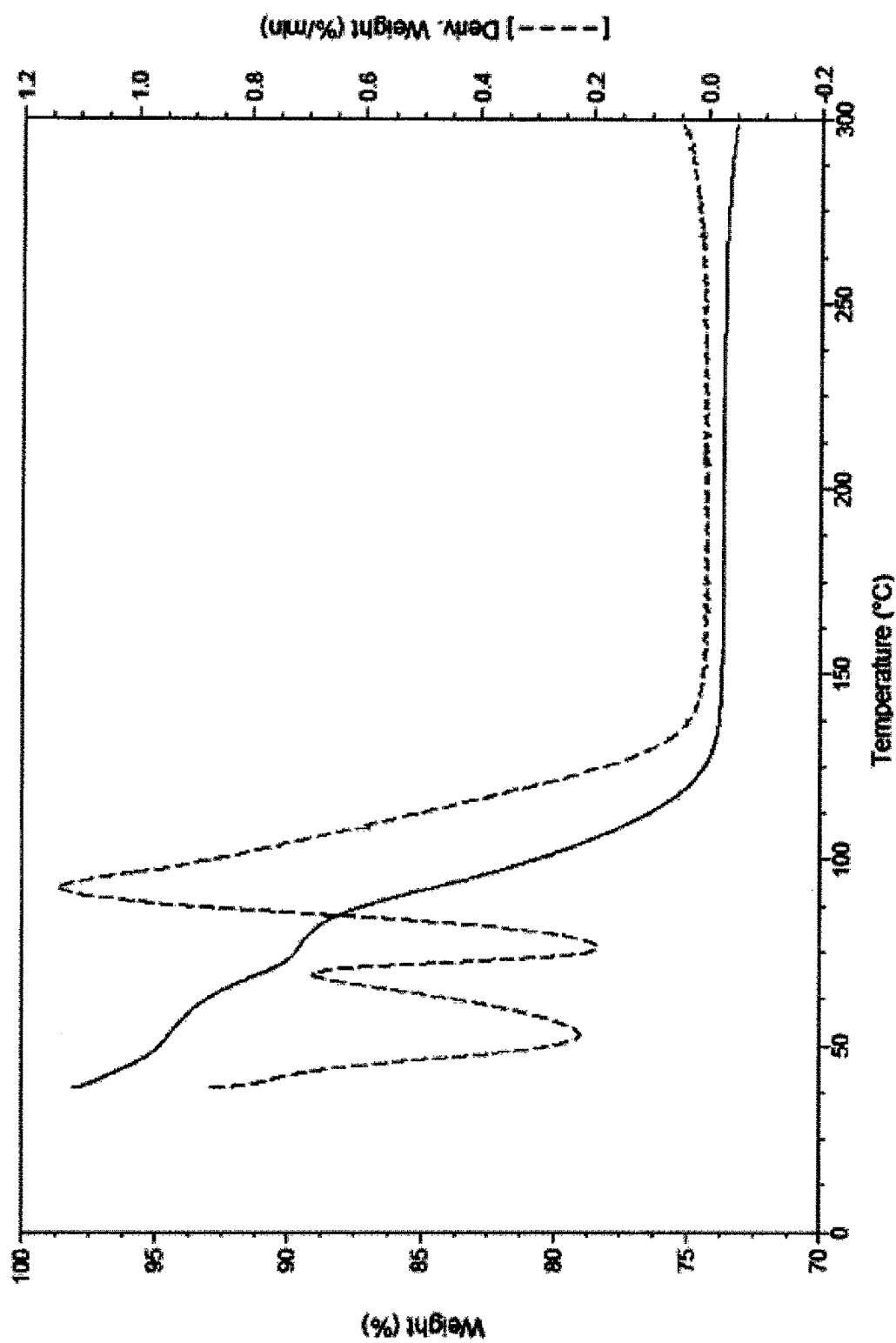
FIGS. 12A and 12B show illustrative graphical representations of TGA of PVBVAVA-TATP microspheres trace (solid) and TGA derivative (dotted) at 2°/min (FIG. 12A) and 20°/min (FIG. 12B)
Figure 12B:
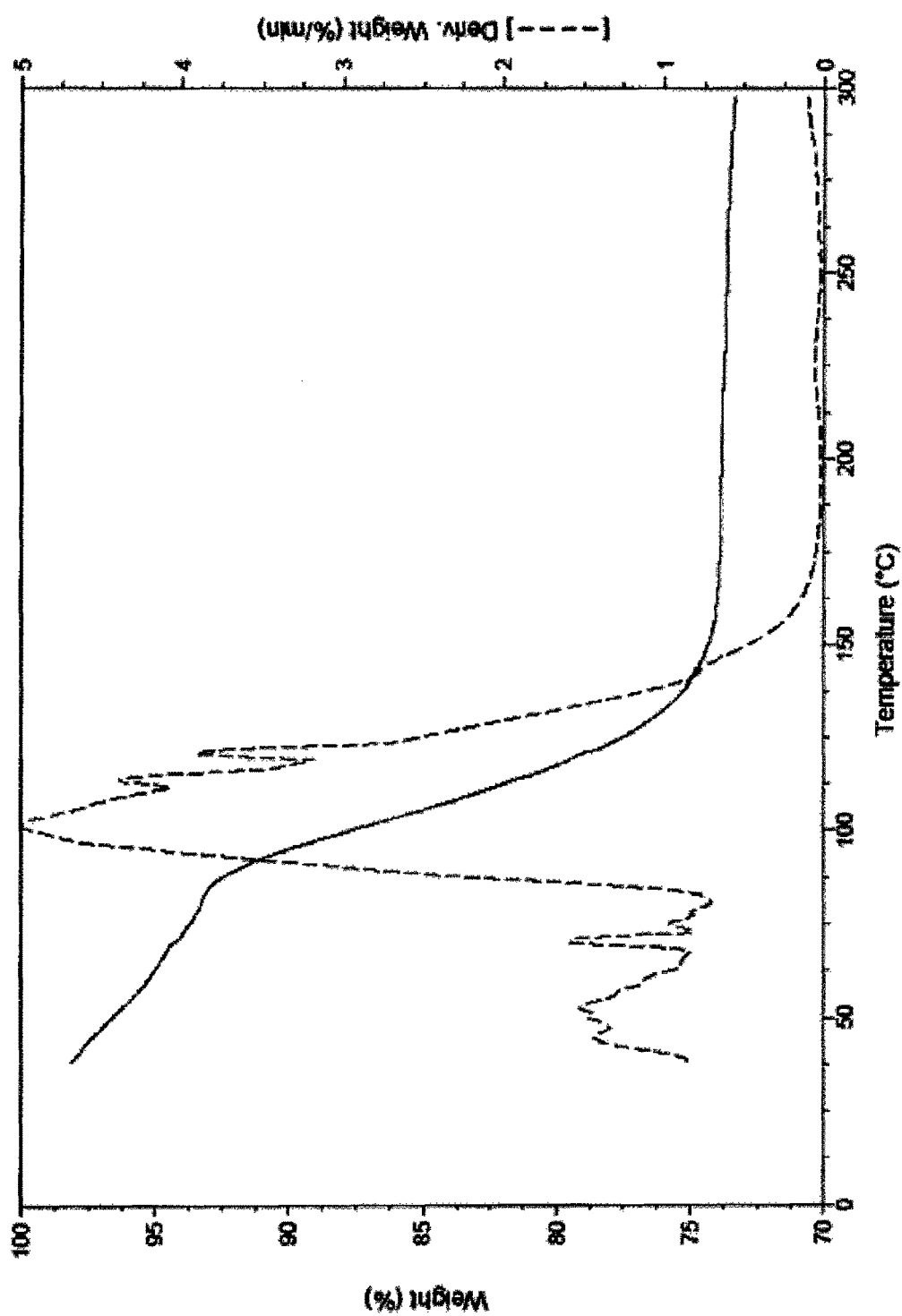
Figure 13:
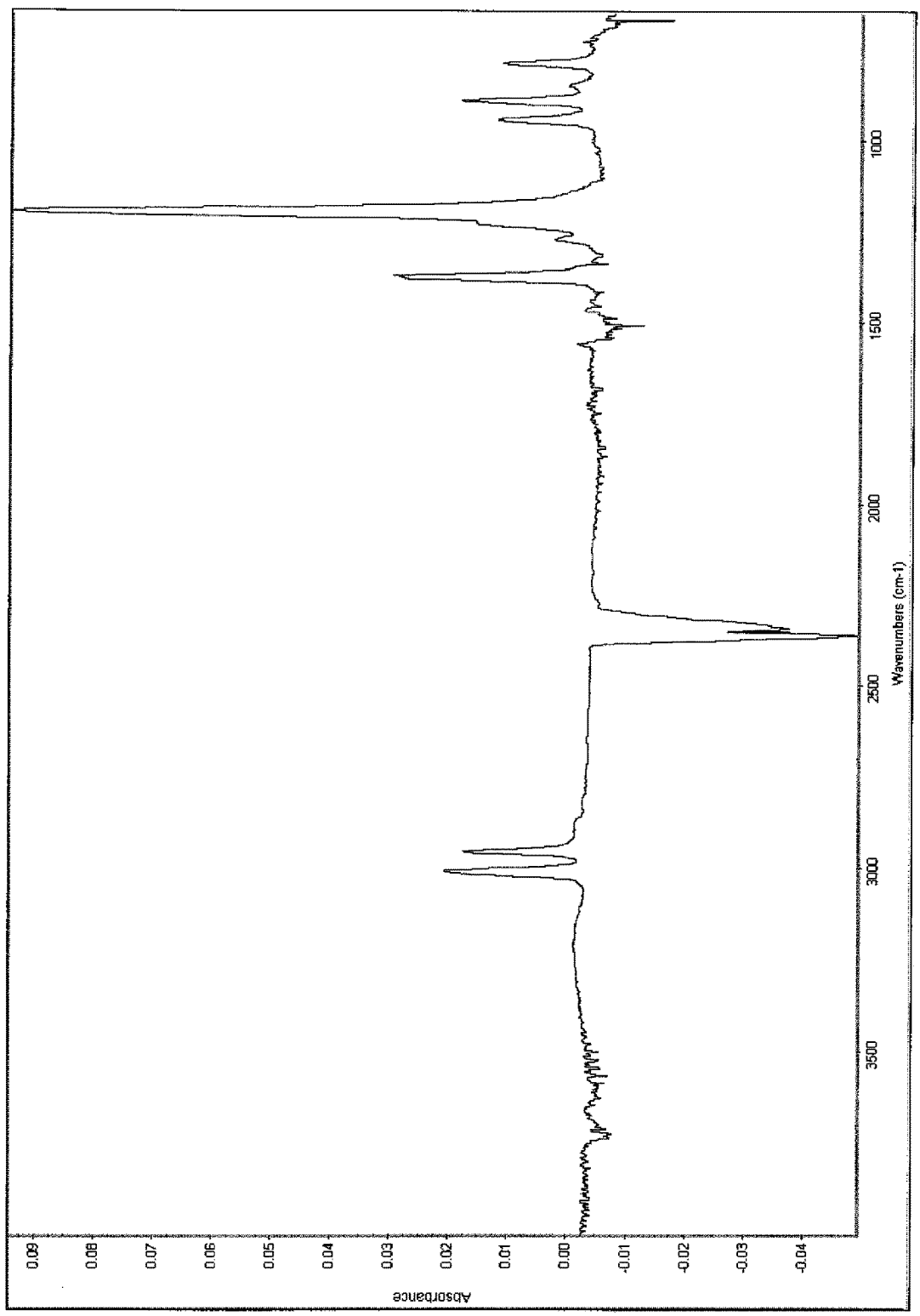
FIG. 13 shows an illustrative graphical representation of IR spectra of TATP from PVBVAVA microspheres.

With regard to the use of poly (vinyl butyral-co-vinyl alcohol-co-vinyl acetate) (PVBVAVA), FIGS. 12A and 12B show illustrative graphical representations of TGA of PVBVAVA-TATP microspheres trace (solid) and TGA derivative (dotted) at 2°/min (FIG. 12A) and 20°/min (FIG. 12B). FIG. 13 shows an illustrative graphical representation of IR spectra of TATP from PVBVAVA microspheres.

Figure 14:
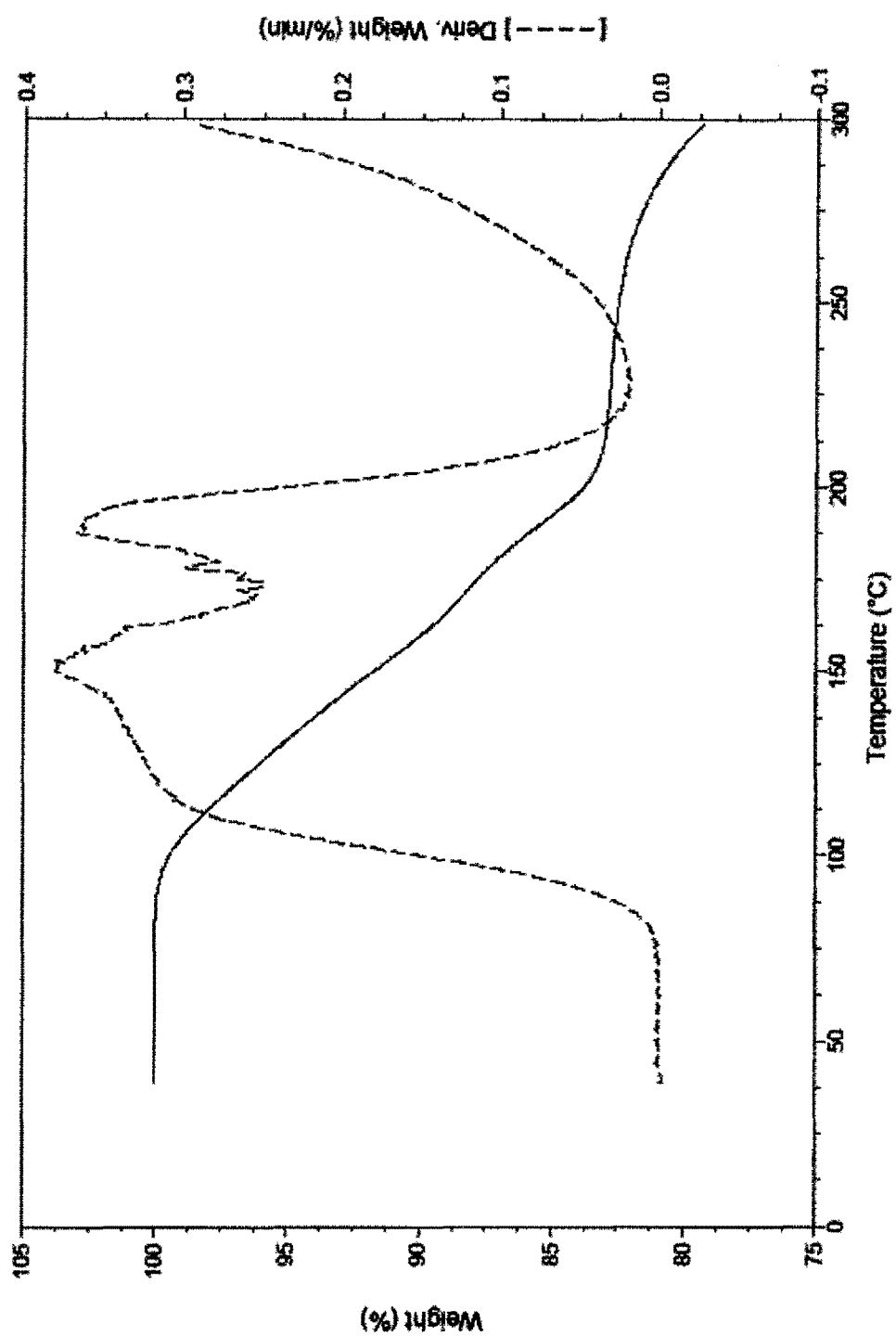
FIG. 14 shows an illustrative graphical representations of TGA of P4MS-TATP microspheres trace (sold) and TGA derivative (dotted line) at 2°/min.
Figure 15:
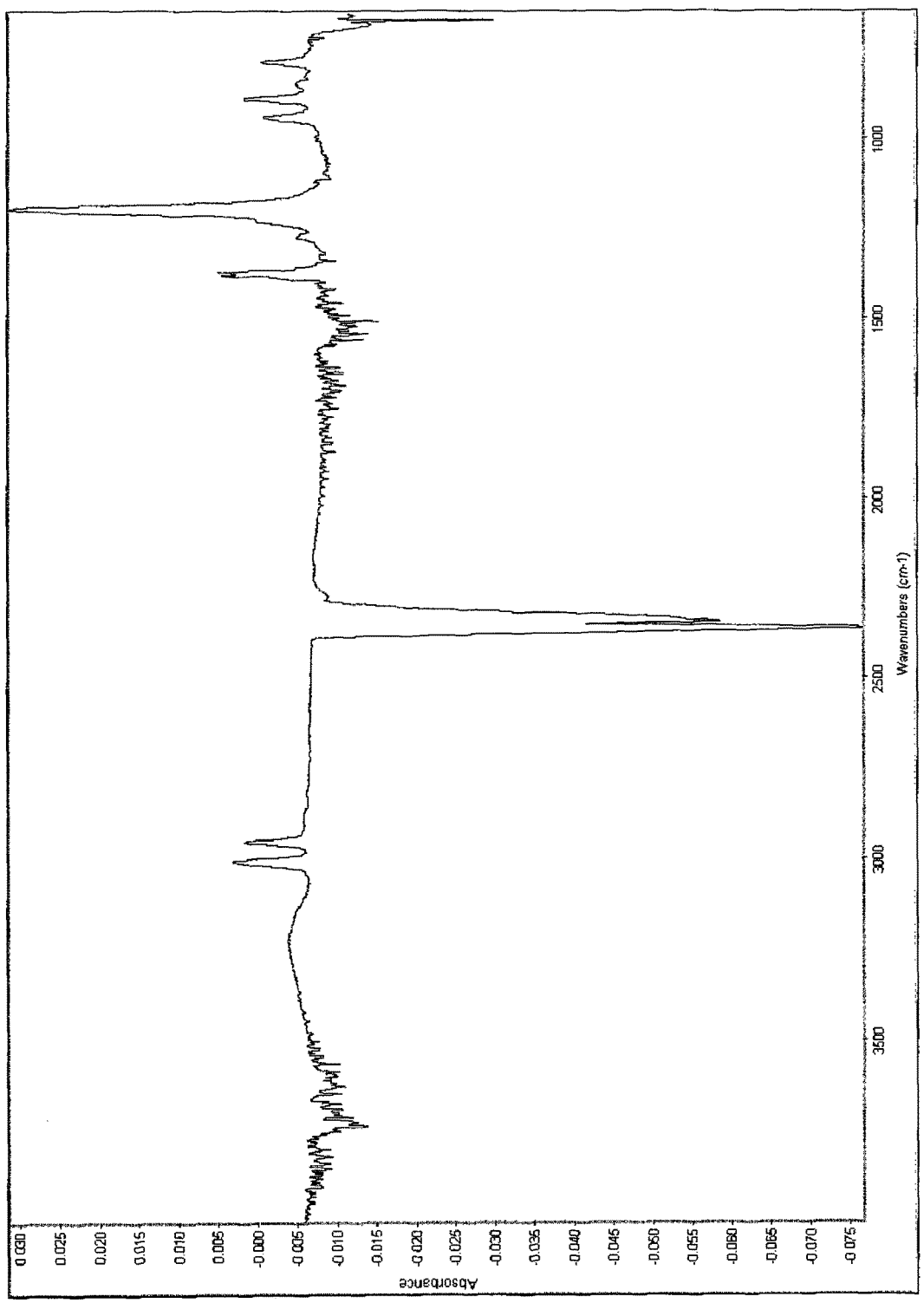
FIG. 15 shows an illustrative graphical representation of IR spectra of TATP from P4MS microspheres.
Figure 16:
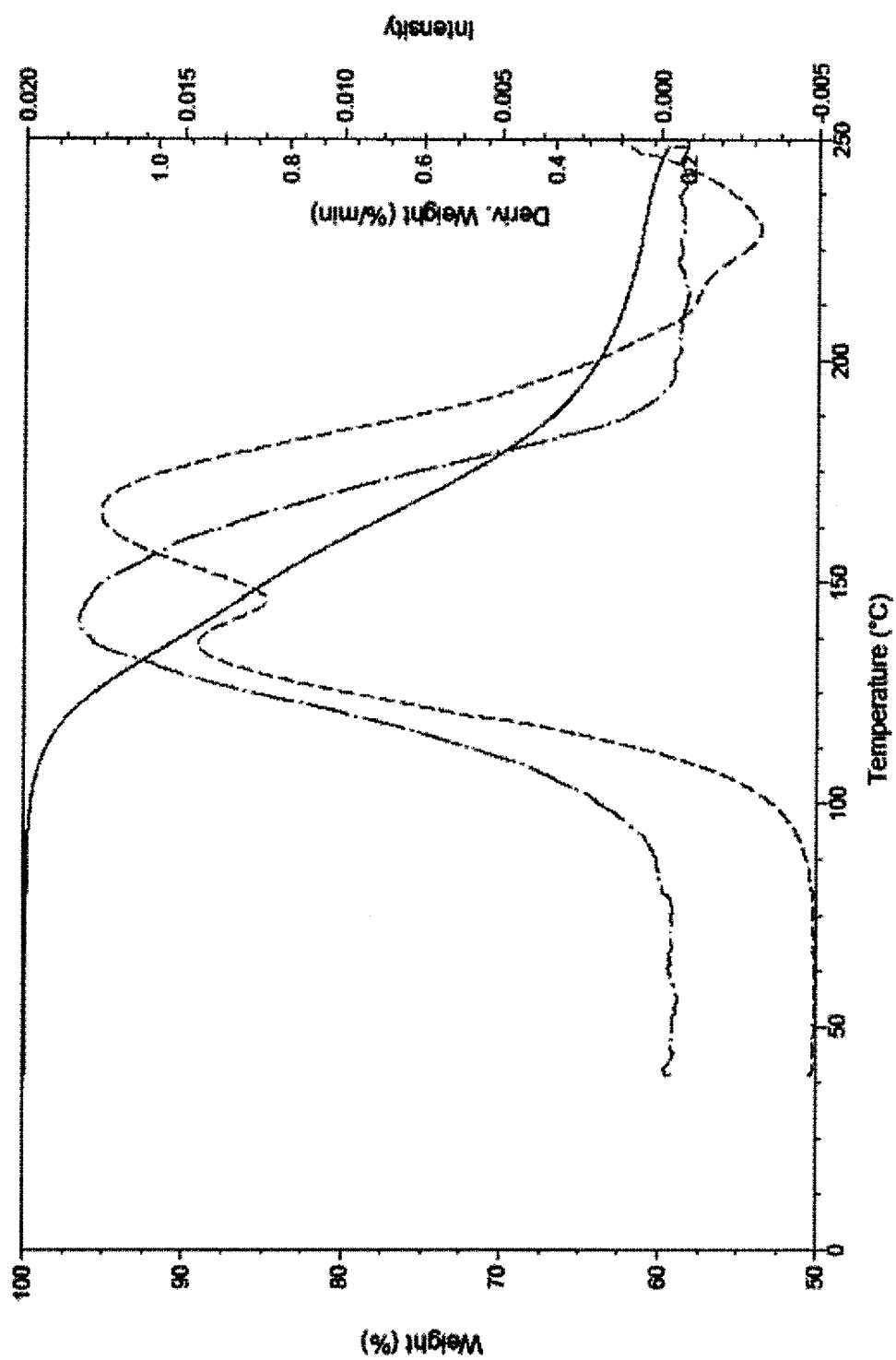
FIG. 16 shows an illustrative graphical representation of YGA of PEM-TATP microspheres trace (solid) and TGA derivative (dotted line), which an 895 $cm^{-1}$ IR signal (dash line) at 2°/min.
Figure 17A:
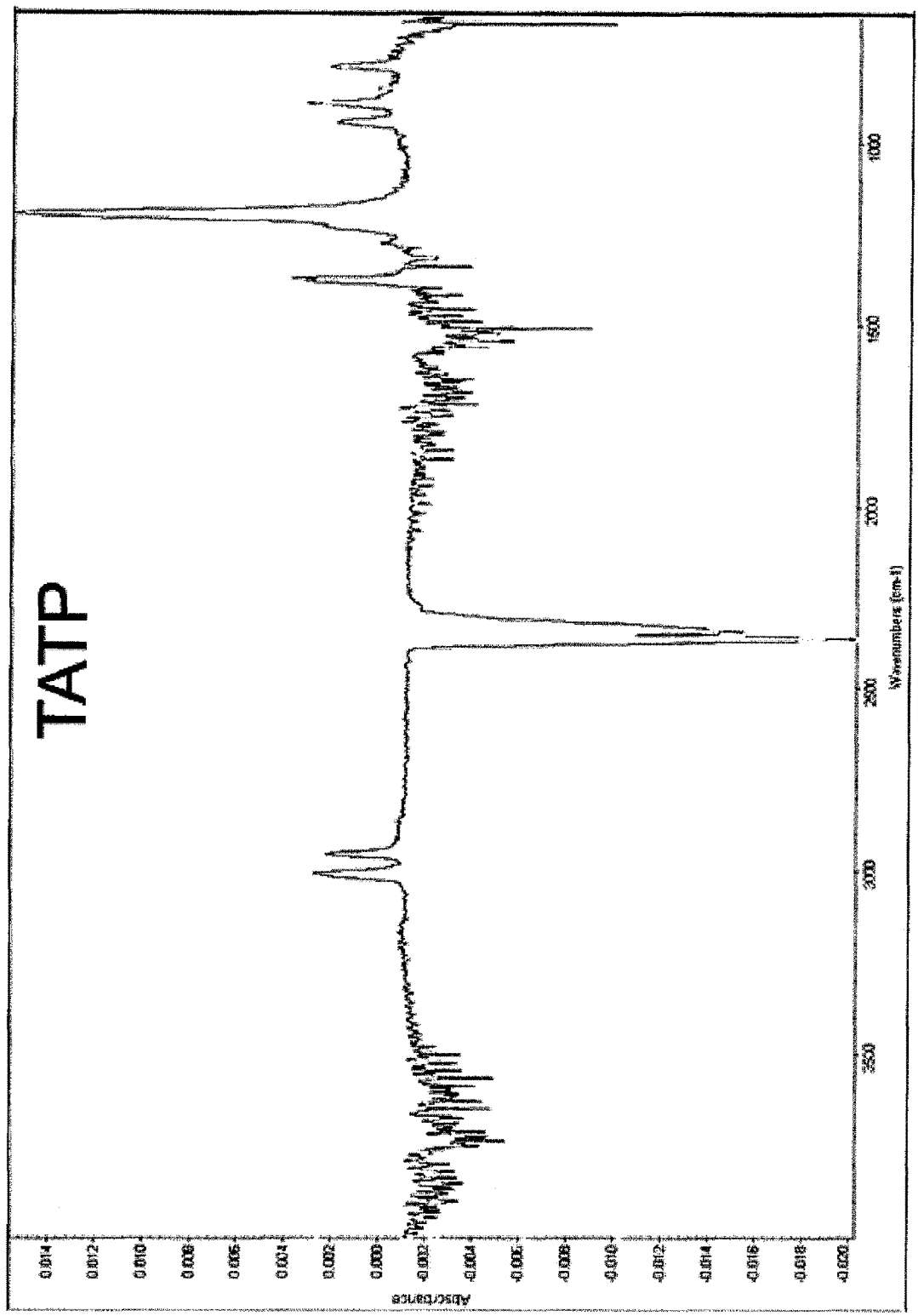
FIGS. 17A and 17B show illustrative graphical representations of IR spectra of TATP from PEM microspheres (FIG. 17A) and mix of PEM decomposition and TATP (FIG. 17B)
Figure 17B:
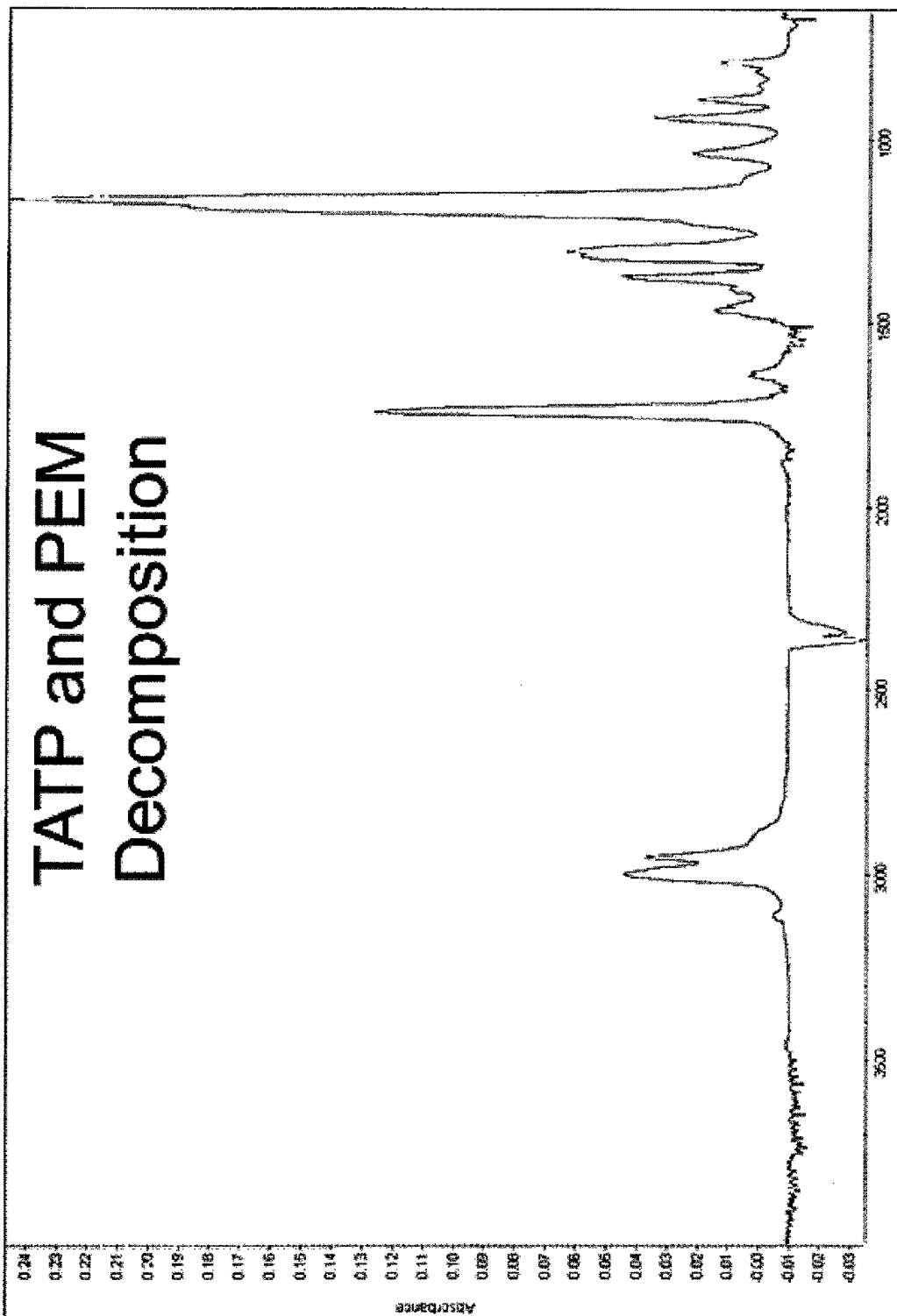

With regard to the use of P4MS, FIG. 14 shows an illustrative graphical representations of TGA of P4MS-TATP microspheres trace (sold) and TGA derivative (dotted line) at 2°/min. FIG. 15 shows an illustrative graphical representation of IR spectra of TATP from P4MS microspheres;

FIG. 16 shows an illustrative graphical representation of YGA of PEM-TATP microspheres trace (solid) and TGA derivative (dotted line), which an 895 $cm^{-1}$ IR signal (dash line) at 2°/min. FIGS. 17A and 17B show illustrative graphical representations of IR spectra of TATP from PEM microspheres (FIG. 17A) and mix of PEM decomposition and TATP (FIG. 17B).

Figure 18:
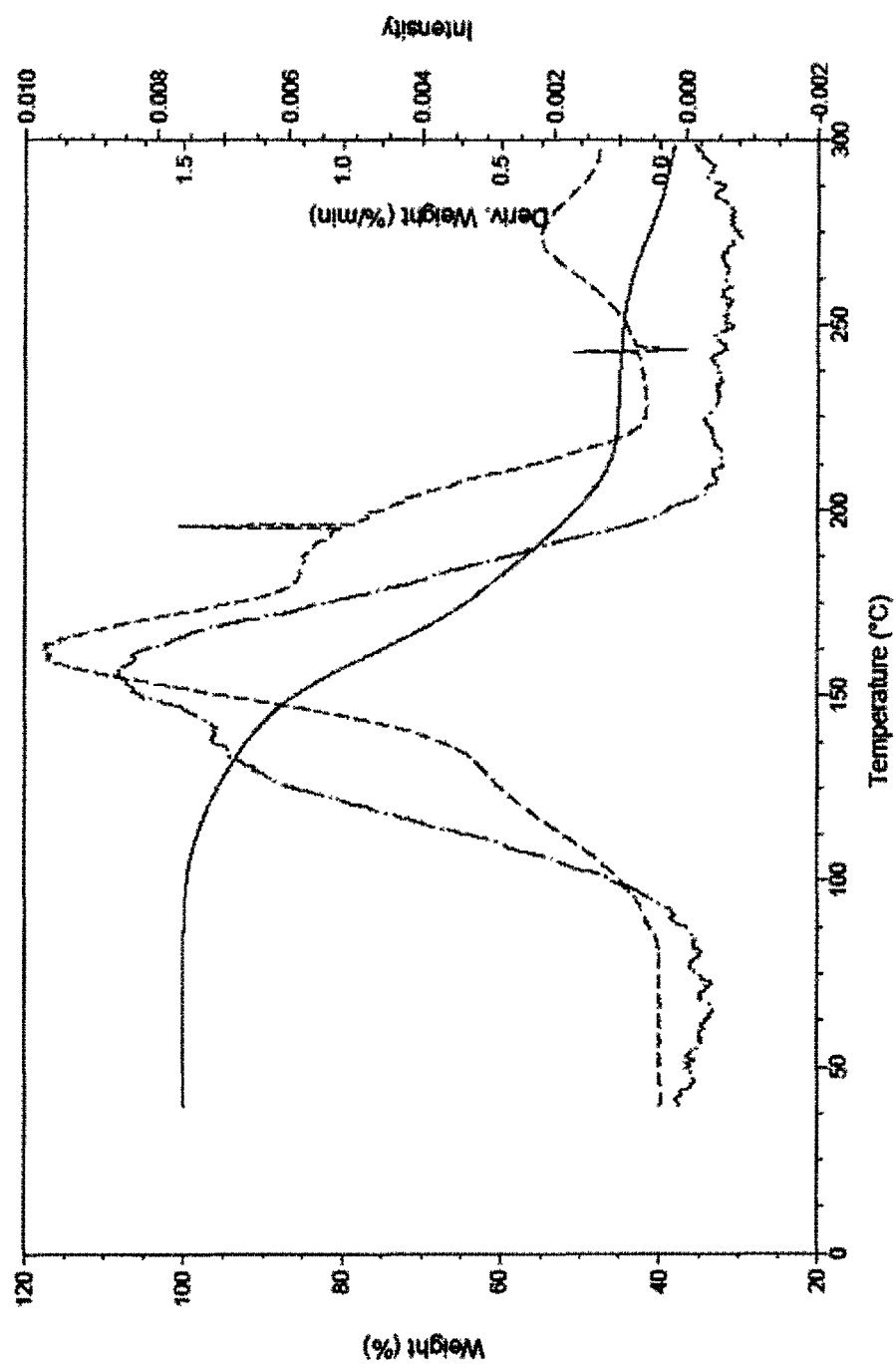
FIG. 18 shows an illustrative graphical representation of PMMA-TATP microspheres trace (solid) and TGA derivative (dotted line) with an 889 $cm^{-1}$ IR signal (dash line) at 2°/min.
Figure 19A:
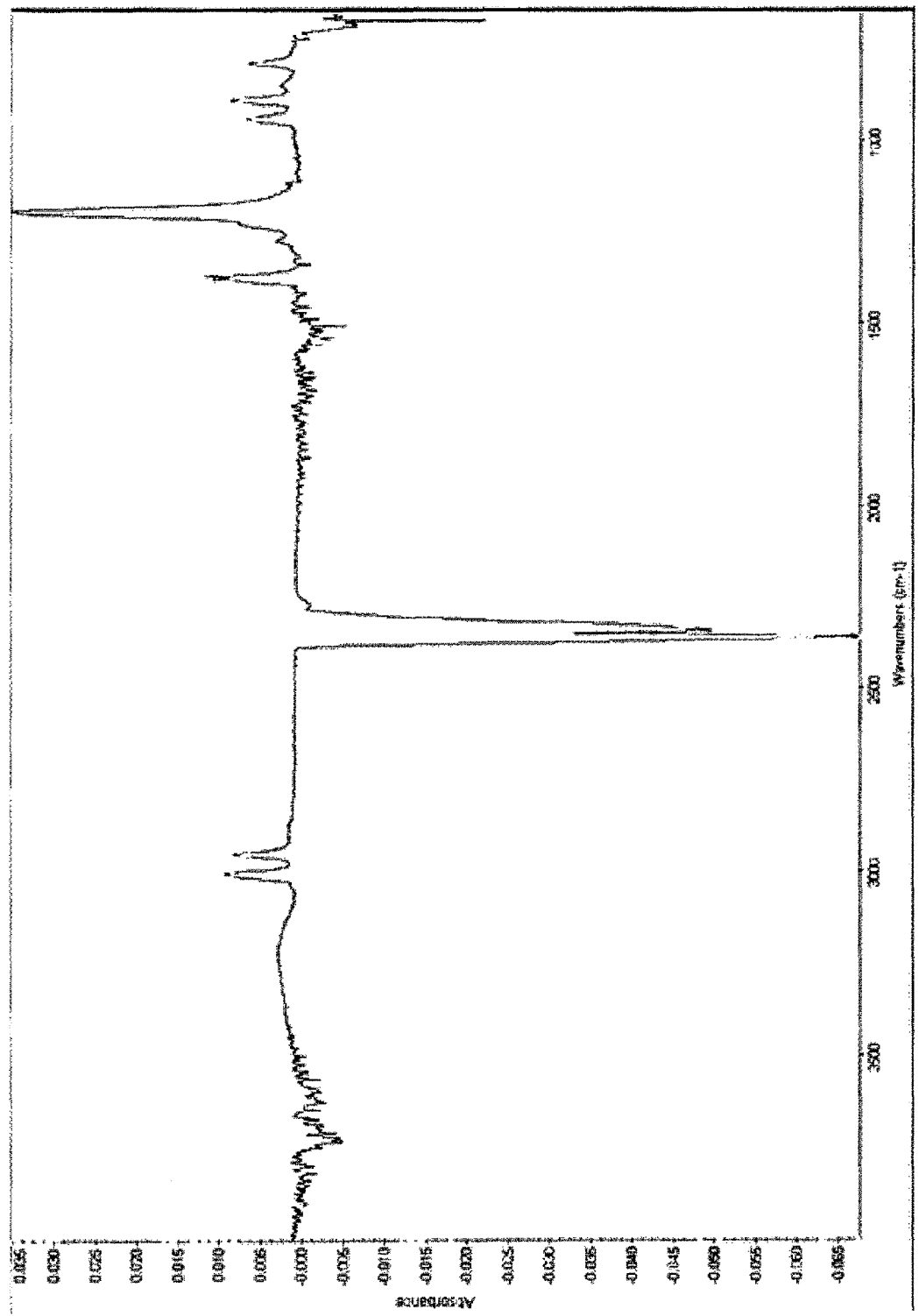
FIGS. 19A and 19B show illustrative graphical representations of IR spectra of TATP from PMMA microspheres (FIG. 19A) and mix of PMMA decomposition and TATP (FIG. 19B)
Figure 19B:
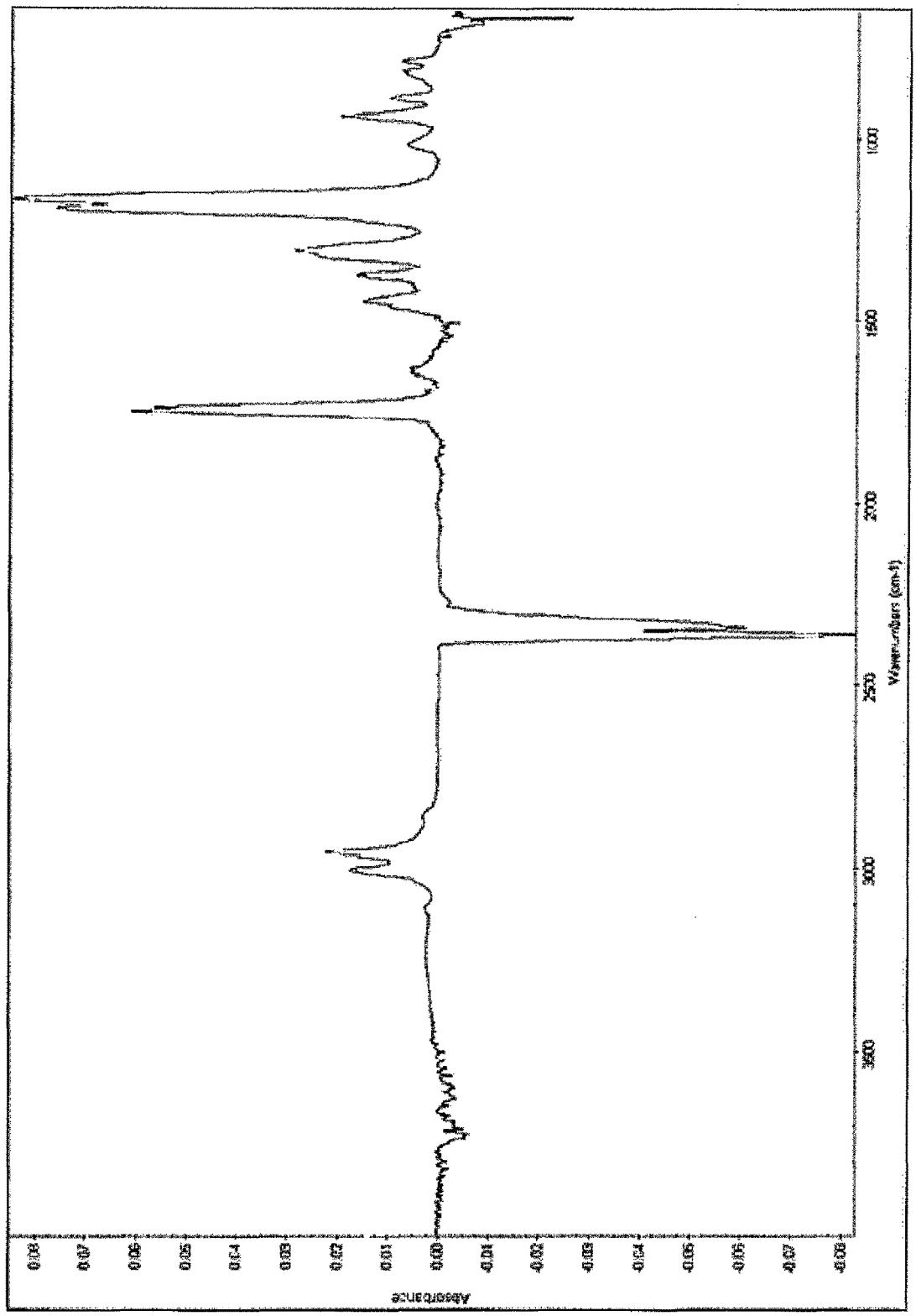
Figure 20:
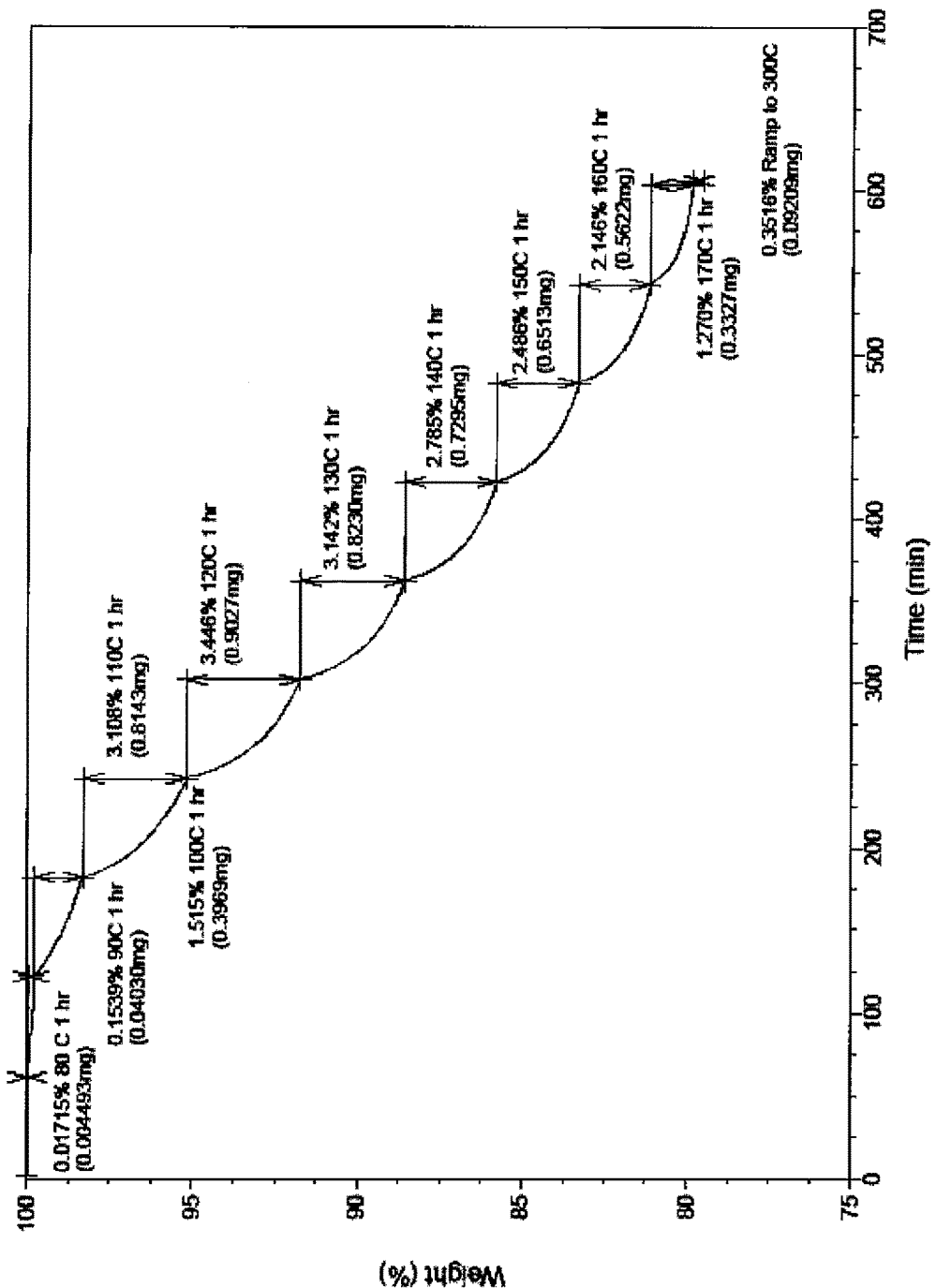
FIG. 20 shows an illustrative graphical representation of a release profile of TATP from polycarbonate.
Figures 1A, 1B:
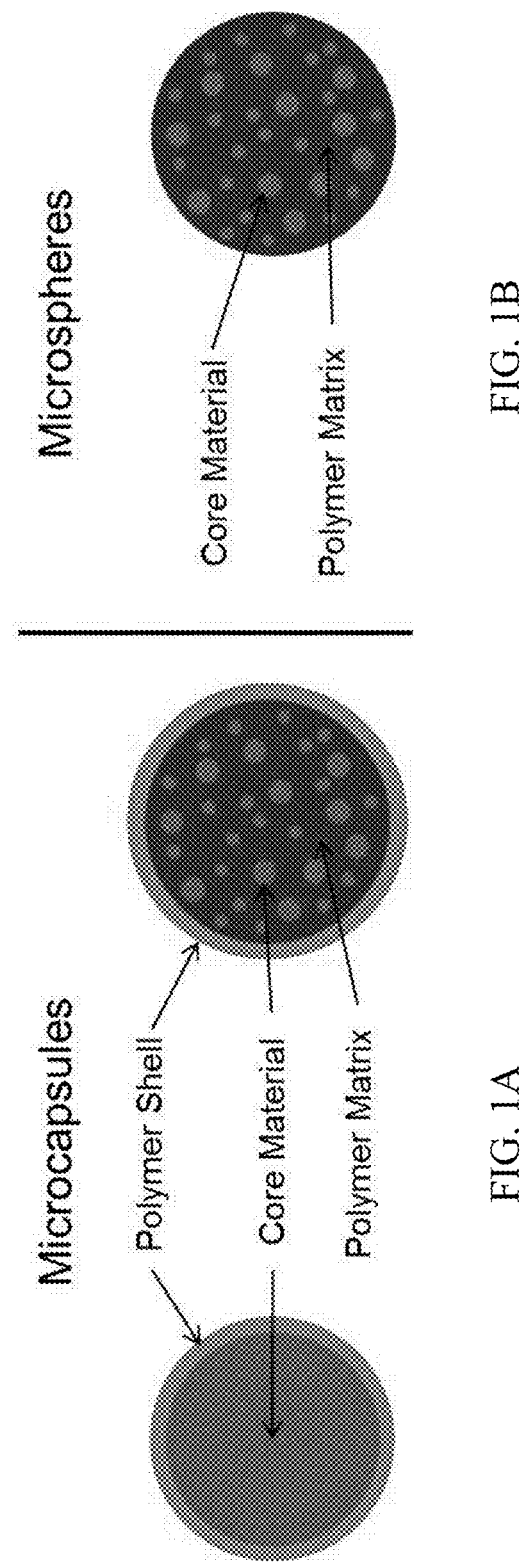

FIG. 18 shows an illustrative graphical representation of PMMA-TATP microspheres trace (solid) and TGA derivative (dotted line) with an 889 $cm^{-1}$ IR signal (dash line) at 2°/min. FIGS. 19A and 19B show illustrative graphical representations of IR spectra of TATP from PMMA microspheres (FIG. 19A) and mix of PMMA decomposition and TATP (FIG. 19B). FIG. 20 shows an illustrative graphical representation of a release profile of TATP from polycarbonate.

General Preparation

In selecting the preferred polymer for encapsulation of the explosive, a number of factors were considered: 1) the polymer must have long-term shelf-life; 2) the release of the core material (explosive) must be pure (type A release)—i.e. not contaminated by release of polymer or polymer decomposition products (type B) or by explosive decomposition products (type C). The solvent evaporation method of encapsulations requires that both the polymer and the core material (the explosive) be soluble in readily removable solvent, i.e. dichloromethane or chloroform, and be insoluble in a second solvent which is immiscible with the first, i.e. water. However, this does not rule out the possible that another method of encapsulation could be used.

The polymer is dissolved in solvent, e.g dichloromethane, chloroform, toluene, ethylacetate. Choice of solvent depends on the mode of creating a capsule. For the emulsion method, the solvent must dissolve both the explosive and polymer. The solvent must not be miscible in water, at least for the microsphere forming technique described here. It must be possible to remove residual solvent from the microspheres at temperature below that where the explosive is released.

The active ingredient (explosive) is added to the solvent with stirring. Creation of the beads is accomplished by adding this mixture to a solution of 2% polyvinyl alcohol (PVA) in water, with vigorous stirring. No specific particle size s desired, a concentration of PVA is selected to yield microspheres 100 µm to 300 µm in size. Experiments determined that 2-4% PVA produced particles that were in this range. The mixture is stirred until all solvent evaporates and beads form. The time required ranged from 1 hour for dichloromethane to 14 hours for toluene. After evaporation of the organic solvent, microspheres are collected by vacuum filtration, rinsed with water, and dried. Residual solvent and explosive on the surface of the microsphere are removed by conditioning the microspheres in an oven. Appropriate temperatures are shown in Table 1 (shown in FIG. 21). The temperature should not be so high that the polymer or explosive decomposes. Heating times were 24 to 48 hours. Heating can be replaced by use of a vacuum desiccation.

By this route, active ingredients TATP, DADP (diacetone diperoxide), HMTD (hexamethylene triperoxide diamine), TNT (2,4,6-trinitrotoluene) and naphthalene were encapsulated.

The loading levels and shelf-stability of the microspheres were investigated using TGA (thermal gravometric analyzer). Purity of the vapor released by the microspheres was determined by examining the off-gases of the TGA by infrared spectrometry (IR) and by GC-MS (gas chromatography coupled to a mass spectrometer). Loading levels of even the most volatile explosive (TATP) were found to remain stable for years. The loss of TATP from the microspheres over time at room temperature was negligible as the data in Table 4 (shown in FIG. 24) shows. Table 3 (shown in FIG. 23) FIG. 23 shows percent TATP and percent mass lost for various samples baked at 80° C. for 24 hours in accordance with an embodiment of the invention.

Analysis of the microspheres was accomplished by TGA-IR to determine at what temperature the evolved vapor was the pure explosive rather than polymer or explosive decomposition (see FIGS. 2A-20).

Example 5: DADP

Diacetone diperoxide (DADP) was encapsulated in polycarbonate and polysulfone by the method outline in examples 1 and 2. The results are shown in Table 2 (shown in FIG. 22).

Example 6: TNT

Polycarbonate shell material (1 g) was added with stirring to 10 mL of the dispersed phase solvent dichloromethane (DCM). Once all the shell material had dissolved 500 mg of the explosive, trinitrotoluene (TNT), was added. When the TNT had completely dissolved in the polymer solution, the entire solution was added to a 2 L beaker containing 200 mL water with 2% of polyvinyl alcohol which was being stirrer at ~900 rpm. This emulsion mixture was allowed to stir until the DCM evaporated allowing the formation of solid plastic microspheres (~1 hr). Additional water (~400 mL) was added with stirring to aid filtration. The solid microspheres were recovered by vacuum filtration. Residual polyvinyl alcohol was removed by further rinsing with distilled water (at least 1 L). The microspheres were dried by under air until they ceased to clump together. The spheres were placed in an open container and baked at 70° C. overnight to remove any remaining solvent.

Practical Application

The intended use of these microspheres was to provide the minute amounts of explosive particulate or vapor for training of bomb sniffing canines or trace explosive detection instrumentation developers. When the explosive vapor is required, the microspheres are to be heated driving the explosive from the polymer matrix. The upper limit of heating is governed by the temperature at which significant decomposition of the polymer or explosive is observed. Most of the polymers cannot be heated above 250° C. without significant decomposition. TATP cannot be heated above 170° C. without significant decomposition. In the case of HMTD if the microencapsulation technique is employed, decomposition of the HMTD is not an issue. The vapor signature of HMTD at room temperature contains only HMTD decomposition products. For this reason Example 4 shows that these products could be for canine training directly, but the encapsulation approach works as well.

The prototype of the device for releasing the explosive vapor is a heater which reaches temperatures up to 250° C. within a few seconds. The microspheres are placed in a small glass or metal cup above which is a top suitable for recondensing the material. Such a top would have a odor free sorbent material such as wire mesh or carbon sponge, and this sorbent material would be suitably above the hot zone to encourage recondensation. Using of 100 mg microspheres and heating at 150° C. for 3 minutes produces sufficient vapor for 30 minutes of canine training. The top with the recondensed material can be removed from the remaining microspheres or the top can be left in place on the microspheres. In either case, the top alone or the entire container should be used at distance from the heat source, at least for the application of canine training. The microspheres can be reheated to produce more explosive vapor for several cycles.

Those skilled in the art will appreciate that numerous modifications and variations may be made to the above disclosed embodiments without departing from the spirit and scope of the present invention.

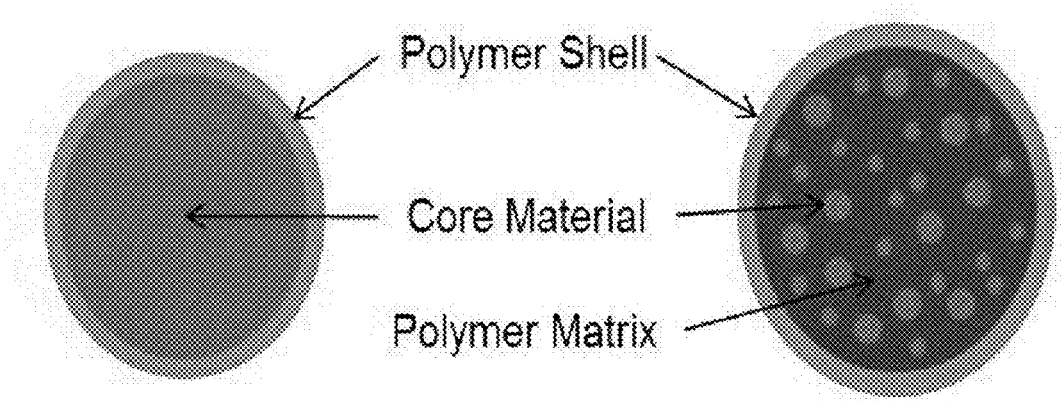

What is claimed is:

1. A method of preparing a non-detonable explosive vapor source comprising the steps of:
   providing a polymer; and
   encapsulating a non-detonable vapor of an explosive using said polymer to provide a non-detonatable matrix, wherein said polymer comprises at least 50% of the non-detonatable matrix, and wherein the encapsulating polymer is a microcapsule including a discrete polymer shell that surrounds a core explosive material.

2. The method of claim 1, wherein the core explosive material includes a predetermined amount of the explosive.

3. The method of claim 1, wherein the microcapsule comprises a predetermined amount of a vapor signature of the explosive.

4. The method of claim 1, wherein the microcapsule encases the explosive in a shell of plastic.

5. The method of claim 4, wherein the plastic comprises any of polystyrenepolystyrene (PS), polysulfone (PSt), polyethylmethacrylate (PEM), poly(lactic-co-glycolic acid) (PLGA), polycarbonate (PC), polyetherimide (PEI), poly(vinyl butyral-co-vinyl alcohol-co-vinyl acetate) (PVBV AV A), or polyethylmethacrylate (PEM).

6. The method of claim 1, wherein the explosive comprises any of triacetone triperoxide (TATP), trinitrotoluene (TNT), Diacetone diperoxide (DADP), hexamethylene triperoxide diamine (HMTD), or naphthalene.

7. A method of preparing a non-detonable explosive vapor source comprising the steps of:
   providing a polymer; and
   encapsulating a non-detonable vapor of an explosive using said polymer to provide a non-detonatable matrix, wherein said polymer comprises at least 50% of the non-detonatable matrix, and wherein the encapsulating polymer is a microcapsule that encapsulates a microsphere-like matrix of polymer and core explosive material.

8. The method of claim 7, wherein the core explosive material includes a predetermined amount of the explosive.

9. The method of claim 7, wherein the microcapsule comprises a predetermined amount of a vapor signature of the explosive.

10. The method of claim 7, wherein the microcapsule encases the explosive in a shell of plastic.

11. The method of claim 10, wherein the plastic comprises any of polystyrenepolystyrene (PS), polysulfone (PSt), polyethylmethacrylate (PEM), poly(lactic-co-glycolic acid) (PLGA), polycarbonate (PC), polyetherimide (PEI), poly(vinyl butyral-co-vinyl alcohol-co-vinyl acetate) (PVBV AV A), or polyethylmethacrylate (PEM).

12. The method of claim 7, wherein the explosive comprises any of triacetone triperoxide (TATP), trinitrotoluene (TNT), Diacetone diperoxide (DADP), hexamethylene triperoxide diamine (HMTD), or naphthalene.

* * * * *

UNITED STATES PATENT AND TRADEMARK OFFICE
CERTIFICATE OF CORRECTION

PATENT NO. : 9,784,723 B1
APPLICATION NO. : 14/215768
DATED : October 10, 2017
INVENTOR(S) : Oxley et al.

Page 1 of 3

It is certified that error appears in the above-identified patent and that said Letters Patent is hereby corrected as shown below:

On the Title Page

Delete the title page and substitute therefore with the attached title page consisting of the corrected illustrative figure(s)

Item (54) and in the Specification, Column 1, Lines 1-3, should read:
SYSTEMS AND METHODS FOR PROVIDING NON-DETONABLE EXPLOSIVES OR EXPLOSIVE SIMULANT SOURCES In the Drawings Please replace FIGS. 1A and 1B with FIGS. 1A and 1B as shown on the attached pages Signed and Sealed this
Nineteenth Day of December, 2017

Joseph Matal
*Performing the Functions and Duties of the
Under Secretary of Commerce for Intellectual Property and
Director of the United States Patent and Trademark Office*

(12) United States Patent
Oxley et al.

(10) Patent No.: US 9,784,723 B1
(45) Date of Patent: Oct. 10, 2017

(54) SYSTEMS AND METHODS FOR PROVIDING NON-DETONATABLE EXPLOSIVES OR EXPLOSIVE STIMULANT SOURCES

(71) Applicant: Board of Governors for Higher Education, State of Rhode Island and Providence Plantations, Providence, RI (US)

(72) Inventors: Jimmie C. Oxley, Narragansett, RI (US); James L. Smith, Narragansett, RI (US); Jonathan N. Canino, Kingston, RI (US)

(73) Assignee: Council on Postsecondary Education, Warwick, RI (US)

( * ) Notice: Subject to any disclaimer, the term of this patent is extended or adjusted under 35 U.S.C. 154(b) by 0 days.

(21) Appl. No.: 14/215,768

(22) Filed: Mar. 17, 2014

Related U.S. Application Data

(60) Provisional application No. 61/790,014, filed on Mar. 15, 2013.

(51) Int. Cl.
  *G01N 31/00* (2006.01)
  *C06B 21/00* (2006.01)
  *G01N 33/22* (2006.01)

(52) U.S. Cl.
  CPC ........ *G01N 33/227* (2013.01); *Y10T 436/10* (2015.01)

(58) Field of Classification Search
  CPC ........ G01N 33/27; G01N 33/52; G01N 31/22; C06B 23/00; C09K 11/00; C09K 11/04
  USPC .................................................. 252/408.1
  See application file for complete search history.

(56) References Cited

U.S. PATENT DOCUMENTS

| | | |
|---|---|---|
| 5,359,936 A | 11/1994 | Simpson et al. |
| 5,413,812 A | 5/1995 | Simpson et al. |
| 5,648,636 A | 7/1997 | Simpson et al. |
| 7,694,628 B2 | 4/2010 | Adebimpe et al. |
| 7,932,089 B2 | 4/2011 | Cohen-Arazi et al. |
| 8,173,430 B2 | 5/2012 | Cohen-Arazi et al. |
| 2005/0016675 A1* | 1/2005 | Bain ............ B60J 10/0088 156/393 |
| 2006/0099247 A1* | 5/2006 | Cantwell ............ A61M 15/00 424/451 |
| 2007/0221087 A1* | 9/2007 | Adebimpe ............ A01K 15/02 102/355 |
| 2009/0194744 A1 | 8/2009 | Adebimpe | 
| 2009/0199936 A1 | 8/2009 | Hagit et al. |

* cited by examiner

*Primary Examiner* — Jill Warden
*Assistant Examiner* — Julie Tavares
(74) *Attorney, Agent, or Firm* — Gesmer Updegrove LLP

(57) ABSTRACT

A non-detonable source of at least one of an explosive or explosive vapor is disclosed, as well as a method of preparing the explosive or explosive vapor that includes the step of mixing the explosive with at least 50% inert material which retains the explosive vapor until heat is applied.

12 Claims, 31 Drawing Sheets